(12) United States Patent
Baker et al.

(10) Patent No.: US 6,897,243 B2
(45) Date of Patent: May 24, 2005

(54) FRUCTOSAMINE OXIDASE: ANTAGONISTS AND INHIBITORS

(75) Inventors: John Richard Baker, Auckland (NZ); Garth J. S. Cooper, Auckland (NZ)

(73) Assignee: Protemix Corporation Limited (NZ)

( * ) Notice: Subject to any disclaimer, the term of this patent is extended or adjusted under 35 U.S.C. 154(b) by 0 days.

(21) Appl. No.: 10/226,685

(22) Filed: Aug. 23, 2002

(65) Prior Publication Data

US 2003/0045506 A1 Mar. 6, 2003

Related U.S. Application Data

(63) Continuation of application No. 09/975,751, filed on Oct. 10, 2001, now Pat. No. 6,610,693, which is a continuation of application No. 09/671,967, filed on Sep. 27, 2000, now Pat. No. 6,348,465.

(30) Foreign Application Priority Data

| Sep. 25, 1998 | (NZ) | 332084 |
| Mar. 3, 1999 | (NZ) | 334471 |
| Aug. 9, 1999 | (NZ) | 337042 |
| Sep. 28, 1999 | (NZ) | 332079 |

(51) Int. Cl.$^7$ ............................................. A61K 31/13
(52) U.S. Cl. ................................................... 514/674
(58) Field of Search ............................... 514/248, 426, 514/562, 565, 762, 674

(56) References Cited

U.S. PATENT DOCUMENTS

| 4,374,829 A | 2/1983 | Harris et al. |
| 4,410,541 A | 10/1983 | Kamimae et al. |
| 4,758,583 A | 7/1988 | Cerami et al. |
| 4,866,090 A | 9/1989 | Hoffman et al. |
| 4,952,568 A | 8/1990 | Sawai et al. |
| 5,077,313 A | 12/1991 | Lubec |
| 5,128,360 A | 7/1992 | Cerami et al. |
| 5,246,970 A | 9/1993 | Williamson et al. |
| 5,387,109 A | 2/1995 | Ishikawa et al. |
| 5,852,009 A | 12/1998 | Cerami et al. |
| 6,348,465 B1 * | 2/2002 | Baker ......................... 514/248 |
| 6,610,693 B2 * | 8/2003 | Baker ......................... 514/248 |

FOREIGN PATENT DOCUMENTS

| AU | 30918/89 A | 9/1989 |
| AU | 80936/94 A1 | 5/1995 |
| AU | 14470/95 A | 7/1995 |
| AU | 41349/96 A1 | 5/1996 |
| DE | 3217071 A1 | 11/1983 |
| EP | 0 426 066 A2 | 5/1991 |
| EP | 0 576 838 | 1/1994 |
| GB | 2192789 A | 1/1988 |
| GB | 2192790 A | 1/1988 |
| JP | 57-144215 A | 9/1982 |
| WO | WO 85/04169 | 9/1985 |
| WO | WO 87/05505 A1 | 9/1987 |
| WO | WO 95/11690 | 5/1995 |
| WO | WO 95/17900 | 7/1995 |
| WO | WO 96/12483 | 5/1996 |
| WO | WO 99/39712 A1 | 8/1999 |
| WO | WO 00/18392 A1 | 4/2000 |
| WO | WO 00.18392 | 4/2000 |
| WO | WO 00/18891 A1 | 4/2000 |

OTHER PUBLICATIONS

Allen, K. G. D. et al. (Jan. 1987). "Tetramine Cupruretic Agents: A Comparison in Dogs," *Am. J. Vet. Res.* 48(1):28–30.

Borthwick, T. R. et al. (Apr. 1980). "Copper Chelating Agents: A Comparison of Cupruretic Responses to Various Tetramines and D–Penicillamine," *J. Lab. Clin. Med.* 95(4):575–580.

Cameron, N. E. and Cotter, M. A. (Aug. 1995). "Neurovascular Dysfunction in Diabetic Rats. Potential Contribution of Autoxidation and Free Radicals Examined Using Transition Metal Chelating Agents," *J. Clin. Invest.* 96(2):1159–1163.

Cameron, N.E. et al. (1995). "Ciliary Neuronotrophic Factor Improves Nerve Conduction and Regeneration in Experimental Diabetes," *Diabetologia* 38(Suppl. 1):A233 Abstract.

Cohen, N. L. et al. (1983). "The Effect of Copper Chelating Drugs on Liver Iron Mobilization in the Adult Rat," *Biochemical and Biophysical Research Communications* 113(1):127–134.

Dwivedi, R. S. et al. (1978). "The Effect of Triethylene Tetramine Upon the Selective Removal of Nickel (II), Iron (II), Manganese (II) and Tin (II) in Rats," *Chemosphere* 11:925–932.

Iseki, K. et al. (1992). "Comparison of Disposition Behavior and De–Coppering Effect of Triethylenetetramine in Animal Model for Wilson's Disease (Long–Evans Cinnamon Rat) with Normal Wistar Rat," *Biopharmaceutics & Drug Deposition* 13:273–283.

Keegan, A. et al. (1996). "Transition Metal Chelators and Anti–Oxidants Prevent the Development of Defective Endothelium–Dependent Relaxation in Aortas from Diabetic Rats," *Diabetic Medicine* 13(Suppl. 1):S17 Abstract.

Keegan, A. et al. (Sep. 27, 1999). "Effects of Chelator Treatment on Aorta and Corpus Cavernosum From Diabetic Rats," *Free Radical Biology & Medicine* 27(5–6):536–543.

(Continued)

*Primary Examiner*—Raymond J. Henley, III
(74) *Attorney, Agent, or Firm*—Buchanan Ingersoll P.C.

(57) ABSTRACT

The present invention relates to methods of treating an individual with diabetes mellitus by administering to said individual an effective amount of copper chelators, hydrazine compounds, and/or substrate analogues. The invention also relates to methods of treating an individual with diabetes mellitus by lessening fructosamine odixase activity in said individual. Provided within is disclosure pertaining to treatment, pharmaceutical compositions, dosage ranges, and uses of fructosamine oxidase enzyme inhibitors to lessen fructosamine oxidase activity.

109 Claims, 5 Drawing Sheets

OTHER PUBLICATIONS

Appelbaum et al., "The Protective Role of Neocuproine Against Cardiac Damage in Isolated Perfused Rat Hearts", *Free Radical Biology & Medicine,* vol. 8, pp. 133–143, 1990; Pergamon Press USA.

Beshgetoor et al., "Clinical conditions altering cooper metabolism in humans", Am J Clin Nutr 1998; 67 (suppl):1017S–21S.

Bingham et al., "Characterization of intracellular copper pools in rat hepatocytes using the chelator diamsar", Am. J. Physiol. 272 (Gastrointest. Liver Physiol. 35): G1400–G1407, 1997.

Brownlee et al., "Aminoguanidine Prevents Diabetes–Induced Arterial Wall Protein Cross–Linking", Science, New Series, vol. 232, No. 4758 (Jun. 27, 1986), 1629–1632.

Bryszewska et al., "Oxidative Processes in Red Blood Cells from Normal and Diabetic Individuals", *Biochemistry and Molecular Biology International,* vol. 37, No. 2, 345–354, Oct. 1995.

Chang et al., "Increased Collagen Cross–Linkages in Experimental Diabetes Reversal by β–Aminopropionitrile and D–Penicillamine", Diabetes, vol. 29, Oct. 1980, 778–781.

Cooper, "The Action of Mebanazine, a Mono Amine Oxidase Inhibitor Antidepressant Drug in Diabetes", Int. J. Neurophyschiatry, 4:342–5(1966).

Dubois et al., "Triethylene Tetramine Dihydrochloride in Wilson's Disease," The Lancet, Oct. 1970.

Ekblom, "Potential Therapeutic Value of Drugs Inhibiting Semicarbazide–Sensitive Amine Oxidase: Vascular Cytoprotection in Diabetes Mellitus", Pharmacological Research, vol. 37, No 2, 1998.

Elling, "Penicillamine, Captopril, and Hypoglycemia", Annals of Internal Medicine, vol. 103, No. 4, Oct. 1985.

Hoffken et al., "Excretion of Zinc in Diabetics Receiving Penicillamine", Z Klin Chem Klin Biochem. Jan. 7, 1969; (1):4–7.

Leinonen et al., "Susceptibility of LDL to oxidation is not associated with the presence of coronary heart disease or renal dysfunction in NIDDM patients", Clinica Chimica Acta 275 (1998) 163–174.

McArdle et al., "Effect of chelators on copper metabolism and cooper pools in mouse hepatocytes," Am. J. Physiol. 256 (Gastrointest. Liver Physiol. 19): G667–G672, 1989.

Norton et al., "Amioguanidine Prevents the Decreased Myocardial Compliance Produced by Streptozotocin–Induced Diabetes Mellitus in Rats", Circulation. 1996;93:1905–1912.

Ou et al., Thioctic (Lipoic) Acid: ATherapeutic Metal–Chelating Antioxidant?, Biochemical Pharmacology, vol. 50, No. 1, pp.123–126. (1995).

Pucheu, et al., "Effect of Iron Overload in the Isolated Ischemic and Reperfused Rat Heart,", *Cardiovascular Drugs and Therapy,* 1993; 7:701–711.

Rogers et al., "Hydrazine Stress in the Diabetic: Ornithine Decarboxylase Activity", Biochemical Medicine and Metabolic Biology, 40, 46–49 (1988).

Salonen et al., Serum Copper and the Risk of Acute Myocardial Infarction: A Prospective Population Study in Men in Eastern Finland, Am. J. Epidemiol, 1991; 134: 268–76.

Saunders, "The Effects of Excess Renal Copper on Kidney Function in the Diabetic Rat", Research Communications in Chemical Pathology and Pharmacology, vol. 52, No. 1, Apr. 1986, 45–49.

Sugimoto et al., "Effects of Aminoguanidine on Structural Alterations of Microvessels in Peripheral Nerve of Streptozotocin Diabetic Rats", Microvascular Research 53, 105–112 (1997).

Tessier et al., "Effect of pH, phosphate and copper on the interaction of glucose with albumin", Glyconjugate Journal 15, 571–574 (1998), U.K.

Vesely et al., "New Strategies in the Prevention and Management of Diabetes and Its Complications," Online Journal, Jacksonville Medicine: May 1997. http://www.onlinejournal.com.

Walter et al, "Copper, Zinc, Manganese, and Magnesium Status and Complications of Diabetes Mellitus", Diabetes Care, vol. 14, No. 11, Nov. 1991.

Wolff et al., "Aminoguanidine Is an Isoform–Selective, Mechanism–Based Inactivator of Nitric Oxide Synthase", Archives of Biochemistry and Biophysics, vol. 316, No. 1, Jan. 10, pp. 290–301, 1995.

Wolff et al., "Inactivation of Nitric Oxide Synthase by Substituted Aminoguanidines and Aminoisothioureas[1]", JPET 283:265–273, 1997.

Wolff, "Diabetes Mellitus and Free Radicals", *The British Council* (1993), vol. 49, No. 3 pp. 642–652.

Yagihashi et al., "Effect of Aminoguanidine on Functional and Structural Abnormalities in peripheral Nerve of STZ–Induced Diabetic Rats", Diabetes, vol. 41, Jan. 1992, 47–52.

Young et al., "The Effects of Desferrioxamine and Ascorbate on Oxidative Stress in the Streptozotocin Diabetic Rat", *Free Radical Biology & Medicine,* vol. 18, No. 5, pp. 833–840, 1995.

Yu et al., "Aminoguanidine inhibits semicarbazide–sensitive amine oxidase activity: implications for advanced glycation and diabetic complications", Diabetologia (1997) 40: 1243–1250.

Kodama, H. et al. (1997). "Metabolism of Administered Triethylene Tetramine Dihydrochloride in Humans," *Life Sciences* 61(9):899–907.

Love, A. et al. (Oct. 24, 1996). "Nerve Function and Regeneration in Diabetic and Galactosaemic Rats: Antioxidant and Metal Chelator Effects," *European Journal of Pharmacology* 314:33–39.

McQuaid, A. and Mason, J. (1990). "A Comparison of the Effects of Penicillamine, Trientine, and Trithiomolybdate on [$^{35}$S]–labeled Metallothionein In Vitro; Implications for Wilson's Disease Therapy," *Journal of Inorganic Biochemistry* 41:87–92.

Pieper, G. M. et al. (1993). "Hydroxyl Radicals Mediate Injury to Endothelium–Dependent Relaxation in Diabetic Rat," *Molecular and Cellular Biochemistry* 122:139–145.

Planas–Bohne, F. (1979). "Influence of Several Chelating Agents on the Excretion and Organ Concentration of Copper in the Rat," *Toxicology and Applied Pharmacology* 50:337–345.

Shimizu, N. et al. (1997). "Age–Related Copper, Zinc, and Iron Metabolism in Long–Evans Cinnamon Rats and Copper–Eliminating Effects of D–Pencillamine and Tienthine–2HCI," *The Journal of Trace Elements in Experimental Medicine* 10:49–59.

Sone, H. et al. (Apr. 1996). "Inhibition of Hereditary Hepatitis and Liver Tumor Development in Long–Evans Cinnamon Rats by the Copper–Chelating Agent Trientine Dihydrochloride," *Hepatology* 23(4):764–770.

Tandon, S. K. et al. (1984). "Effect of Metal Chelators on Excretion and Tissue Levels of Essential Trace Elements," *Environmental Research* 35:237–245.

Yoshii, J. et al. (2001). "The Copper–Chelating Agent, Trientine, Suppresses Tumor Development and Angiogenesis in the Murine Hepatocellular Carcinoma Cells," *Int. J. Cancer* 94:768–773.

Armbruster, D.A.. (1987). "Fructosamine: Structure, Analysis, and Clinical Usefulness," *Clinical Chemistry*. 33(12):2153–2163.

Gerhardinger, C. et al. (1995). "Novel Degradation of Pathway of Glycated Amino Acids into *Free* Fructosamine by a *Pseudomonas* sp. Soil Strain Extract," *Journal of Biological Chemistry*. 270(1):218–224.

Gillery, P. et al. (1988). "Glycation of Proteins as a Source of Superoxides," *Diabete & Metabolisme*. 14(1):25–30.

Green, T. and Shangguan, X. (1993). "Stoichoimetry of $O_2$ Metabolism and NADPH Oxidation of the Cell–Free Latent Oxidase Reconstituted from Cytosol and Solubilized Membrane from Resting Human Neutrophils," *J. Biol. Chem.* 268(2): 857–861.

Laight, D.W. et al. (1997). "Microassay of Superoxide Anion Scavenging Activity in Vitro," *Environmental Toxicology and Pharmarcology*. 3:65–68.

Takahashi, M. et al. (1997). "Isolation, Purification, and Characterization of Amadoriase Isoenzymes (Fructosyl Amine–oxygen Oxidoreductase EC 1.5.3) from *Aspergillus* sp.," *Journal of Biological Chemistry*. 272(6):3427–3443.

Takahashi, M. et al. (1997). "Molecular Cloning and Expression of Amadoriase Isoenzyme (Fructosyl Amine:Oxygen Oxidoreductase, EC 1.5.3) from *Aspergillus fumigatus*," *Journal of Biological Chemistry*. 272(19): 12505–12507.

Yoshida, N. et al. (1995). "Distribution and Properties of Fructosyl Amino Acid Oxidase in Fungi," *Applied and Environmental Microbiology*. 61(12): 4487–4489.

American Diabetes Association. (1997). "Report of the Expert Committee on the Diagnosis and Classification of Diabetes Mellitus," *Diabetes Care* 20:1183–1197.

American Diabetes Association. (1998). "Economic Consequences of Diabetes Mellitus in the U.S. in 1997," *Diabetes Care* 21(2):296–309.

Anaja, (1997). "Diagnostic performance of red cell sorbitol assay in a Nigerian teaching hospital," *Clinica Chimica Acta*. 262:1–11.

Baker, et al. (1993). "Mechanism of fructosamine assay: evidence against role of superoxide as intermediate in nitroblue tetrazolium reduction," *Clin. Chem.* 39(12):2460–2465.

Barthelmebs, M. et al. (1990). "L–Dopa and Streptozotocin–Induced Diabetic Nephropathy in Rats," *American Journal of Hypertension* 3(6) Part 2:72S–74S.

Barthelmebs, M. et al. (1991). "Effects of Dopamine Pro-drugs and Fenoldopam on Glomerular Hyperfiltration in Streptozotocin–Induced Diabetes in Rats," *Journal of Cardiovascular Pharmacology* 18(2):243–253.

Barthelmebs, M. et al. (1995). "Pathophysiological Role of Dopamine in the Kidney: Effects in Diabetes Mellitus and after Contralateral Nephrectomey," *Hypertens. Res.* 18(Suppl. I):S131–S136.

Baynes, J.W. (1991). "Role of Oxidative Stress in Development of Complications in Diabetes," *Diabetes* 40:405–412.

Boiadzhieva, N. (1990). "The Effect of Dopaminergic Pharmocological Agents on the Pancreatic Islet Apparatus in Rats," *Eksp Med Morfol* 29(3):20–26. (English abstract).

Borgstrom, L. et al. (1986). "Pharmacokinetics of N–Acetylcysteine in Man," *Eur J Clin Pharmacol* 31:217–222.

Chan, P.C. and Bielski, B.H.J. (1974). "Enzyme–catalyzed Free Radical Reactions with Nicotinamide Adenine Nucleotides," *J Biol Chem* 249(4):1317–1319.

Chan, P. C. and Bielski, B.H.J. (1980). "Glyceraldehyde–3–Phosphate Dehydrogenase–catalyzed Chain Oxidation of Reduced Nicotinamide Adenine Dinucleotide by Perhydroxyl Radicals," *J Biol Chem* 255(3):874–876.

Chaturvedi, N. et al. (1998). "Effect of Lisinopril on Progression of Retinopathy in Normotensive People with Type I Diabetes," *The Lancet* 351:28–31.

Dahlman, et al. (2000). "Long–term treatment of Wilson's disease with triethylene tetramine dihydrochloride (trientine)," *QJM* 88(9):609–616.

Deckert T. et al. (1978). "Prognosis of Diabetics with Diabetes Onset before the Age of Thirtyone," *Diabetologia* 14:363–370.

Dubois, R.S. et al. (1970). "Triethylene Tetramine Dihydrochloride in Wilson's Disease," *Lancet* 2(7676):775.

Duchin, K.L. et al. (1988). "Pharmacokinetics of Captopril in Healthy Subjects and in Patients with Cardiovascular Diseases," *Clin. Pharmacokinetics* 14:241–259.

Elstner, E.F. and Heupel, A. (1976). "Inhibition of Nitrite Formation from Hydroxylammonium–.chloride: A Simple Assay for Superoxide Dismutase," *Anal Biochem* 70:616–620.

Epstein, O. and Sherlock, S. (1980). "Triethylene Tetramine Dihydrochloride Toxicity in Primary Biliary Cirrhosis," *Gastroenterology* 78(6):1442–1445.

Executive Committee of the International Union of Biochemistry, ed. (1979). *Enzyme Nomenclature, Recommendations of the Nomenclature Committee of the International Union of Biochemistry*, Academic Press, London, pp. 19–22. (Table of Contents).

Gennaro, A.R. ed. (1990). *Remington's Pharmaceutical Sciences*. 18th edition. Mack Publishing Company: Easton, Pennsylvania, 5 pages. (Table of Contents).

Gerhardinger, C. et al. (1995). "Novel Degradation Pathway of Glycated Amino Acids into *Free* Fructosamine by a *Pseudomonas* sp. Soil Strain Extract," *J Biol Chem* 270(1):218–224.

Greenman, D. et al. (1996). "Subchronic toxicity of triethylenetetramine dihydrochloride in B6C3F1 mice and F344 rats," *Fundam. Appl. Toxicol.* 29(2):185–193.

Greenstock, C.L. and Ruddock, G.W. (1976). "Determination of Superoxide ($O_2$) Radical Anion Reaction Rates Using Pulse Radiolysis," *Int J Radiat Phys Chem* 8:367–369.

Halliwell, B. (1976). "An Attempt to Demonstrate a Reaction between Superoxide and Hydrogen Peroxide," *FEBS Lett* 72(1):8–10.

Halliwell, B. and Gutteridge, J.M.C. (1989). "Free Radicals in Biology and Medicine," Clarendon Press, Oxford, pp. 136–176.

Haslam, R.H. et al. (1980). "Treatment of Wilson's Disease with Triethylene Tetramine Dihydrochloride," *Dev Pharmacol Ther* 1(5):318–324.

Holdiness M.R. (1991). "Clinical Pharmacokinetics of N–Acetylcysteine," *Clin Pharmacokinet* 20(2):123–134.

Horiuchi, T. et al. (1989). "Purification and Properties of Fructosyl–amino Acid Oxidase from *Corynebacterium* sp. 2–4–1," *Agric Biol Chem* 53(1):103–110.

Ido, Y. et al. (1996). "Interactions between the Sorbitol Pathway, Non–enzymatic Glycation, and Diabetic Vascular Dysfunction, " *Nephrol Dial Transplant* 11 [Suppl 5]:72–75.

Karlsson, K. and Marklund, S.L. (1987). "Heparin–induced Release of Extracellular Superoxide Dismutase to Human Blood Plasma," *Biochem J* 242:55–59.

Kashihara, N. et al. (1992). "Selective Decreased de novo Synthesis of Glomerular Proteoglycans under the Influence of Reactive Oxygen Species," *Proc Natl Acad Sci USA* 89:6309–6313.

Klein, R. et al. (1985). "Retinopathy in Young–onset Diabetic Patients," *Diabetes Care* 8(4):311–315.

Kodama, H. et al. (1997). "Metabolism of Administered Triethylene Tetramine Dihydrochloride in Humans," *Life Sci* 61(9):899–907.

Marklund, S.L. et al. (1982). "Superoxide Dismutase in Extracellular Fluids," *Clin Chimica Acta* 126:41–51.

Mattock, M.B. et al. (1998). "Microalbuminuria and Coronary Heart Disease in NIDDM: An Incidence Study," *Diabetes* 47:1786–1792.

McCord, J. M. and Fridovich, I. (1969). "Superoxide Dismutase: An Enzymic Function for Erythrocuprein (Hemocuprein)," *J Biol Chem* 244(22):6049–6055.

Misra, H.P. and Fridovich, I. (1972). "The Role of Superoxide Anion in the Autoxidation of Epinephrine and a Simple Assay for Superoxide Dimutae," *J Biol Chem* 247(10):3170–3175.

Misra, H.P. and Fridovich, I. (1977). "Superoxide Dismutase: 'Positive' Spectrophotometric Assays," *Anal Biochem* 79:553–560.

Mizobuchi, N. et al. (1993). "Serum Superoxide Dimutase (SOD) Activity in Diabetes Mellitus," *Rinsho Byori* 41:673–678. (English abstract).

Mogensen, C.E. and Christensen, C.K. (1984). "Predicting Diabetic Nephropathy in Insulin–dependent Patients," *New Eng J Med* 311(2):89–93.

Mogensen, C.E. et al. (1992). "Microalbuminuria in Non–insulin–dependent Diabetes," *Clin Nephrol* 38 (suppl 1):S28–S38.

Morita J. et al. (1992). "Wilson's disease treatment by triethylene tetramine dihydrochloride (trientine, 2HCl): long–term observations," *Dev. Pharmacol. Ther.* 19(1):6–9.

Morpurgo, L. et al. (1990). "The Role of Copper in Bovine Serum Amine Oxidase," *Biol. Metals* 3:114–117.

Muchova, J., et al. (1999). "Antioxidant systems in polymorphonuclear leucocytes of Type 2 diabetes mellitus," *Diabet Med.* 16(1):74–78.

Muruganandam A. et al. (1994). "ELISA for In Vivo Assessment of Nonenzymatically Glycated Platelet Glutathione Peroxidase," *Clin. Biochem.* 27(4):293–298.

Obach, R. et al. (1984). "The Pharmacokinetic Profile of Carbidopa in Dogs," *J Pharm Pharmacol* 36:415–416.

Palcic, M.M. and Janes, S.M. (1995). "Spectrophotometric Detection of Topa Quinone," *Meth Enzymol* 258:34–38.

Pappert, E.J. et al. (1997). "The Stability of Carbidopa in Solution," *Movement Disorders* 12(4):608–623.

Picard, S. et al. (1996). "Minimally Oxidised LDL as Estimated by a New Method Increase in Plasma of Type 2 Diabetic Patients with Atherosclerosis of Nephropathy," *Diabetes and Metabolism* 22(1):25–30.

Robbins, S.L. et al. (1984). "Pathologic Basis of Disease," $^{rd}$ ed., W.B. Saunders Company: Philadelphia, pp. 991–1061.

Saeki, H. et al. (1998). "Malignant Syndrome Associated with Disseminated Intravascular Coagulation and a High Level of Amylase in Serum, Followed by Diabetic Coma in an Elderly Patient with Parkinson's Disease during L–Dopa Therapy," *Nippon Ronen Igakkai Zasshi* 35(2):139–144. (English abstract).

Saxena, A.K. et al. (1996). "Purification and Characterization of a Membrane–bound Deglycating Enzyme (1–Deoxyfructosyl Alkyl Amino Acid Oxidase, EC 1.5.3) from a *Pseudomonas* sp. Soil Strain," *J Biol Chem* 271(51):32803–32809.

Siegemund R. et al. "Mode of action of triethylenetetramine dihydrochloride on copper metabolism in Wilson's disease," *Acta. Neurol. Scand.* 83(6):364–366. (No date Available).

Skrha, J. et al. (1996). "Relationship of Oxidative Stress and Fibrinolysis in Diabetes Mellitus.," *Diabet. Med.* 13(9):800–805.

Smith, P.R. and Thornalley, P.J. (1992). "Mechanism of the degradation of non–enzymatically glycated proteins under physiological conditions. Studies with the model fructosamine, $N_\epsilon$–(1–deoxy–D–fructos–1–yl)hippuryl–lysine," *Eur. J. Biochem.* 210(3):729–739.

Smith, S.A. and Pogson, C.I. (1977). "Trytophan and the Control of Plasma Glucose Concentrations in the Rat," *Biochem J* 168(3):495–506.

Somani, B., et al. (1999). "Elimination of superoxide dismutase interference in fructosamine assay, " *Clin. Biochem.* 32(3):185–188.

Sone, H. et al. (1996). "Inhibition of Hereditary Hepatitis and Liver Tumor Development in Long–Evans Cinnamon Rats by the Copper–Chelating Agent Trientine Dihydrochloride," *Hepatology* 23(4):764–770.

Sugimoto, H. et al. (1999). "Advanced glycation end products–cytokine–nitric oxide sequence pathway in the development of diabetic nephropathy: aminoguanidine ameliorates the overexpression of tumour necrosis factor–alpha and inducible nitric oxide synthase in diabetic rat glomeruli," *Diabetologia* 42(7):878–886.

Talseth, T. (1976). "Studies on Hydralazine," *European Journal of Clinical Pharmacology* 10(6):395–401.

Talseth, T. (1977). "Kinetics of Hydralazine Elimination," *Clinical Pharmacology Therapeutics* 21(6):715–720.

Tanabe, R. et al. (1996). "Uptake Mechanism of Trientine by Rat Intestinal Brush–border Membrane Vesicles," *J Pharm Pharmacol* 48:517–521.

The Diabetes Control and Complications Trial Research Group. (1993). "The Effect of Intensive Treatment of Diabetes on the Development and Progression of Long–term Complications in Insulin–dependent Diabetes Mellitus," *N Eng J Med.* 329(14):977–986.

UKPDS Study Organisation. (1998). "Intensive Blood–glucose Control with Sulphonylureas or Insulin Compared with Conventional Treatment and Risk of Complications in Patients with Type 2 Diabetes (UKPDS 33)," *Lancet* 352:837–853.

Vailly, B. et al. (1990). "Prevention of L–dopa of Early Renal Consequences of Diabetes Induced by Strepotozocin in Rats,"*Arch Mal Coeur Vaiss* 83(8):1259–1262. (English abstract).

Walshe, J.M. (1973). "Cooper Chelation in Patients with Wilson's Disease: A Comparison of Penicillamine and Triethylene Tetramine Dihydrochloride," *Q J Med* New Series, XLII(167):441–452.

Walshe, J.M. (1982). "Treatment of Wilson's Disease with Trientine (Triethylene Tetramine) Dihydrochloride," *Lancet* 8273:643–647.

Witztum, J.L. (1993). "Role of Oxidised Low Density Lipoprotein in Atherogenesis," *Br Heart J* 69 (Suppl):S12–S18.

Wolff, S.P. et al. (1991). "Protein Glycation and Oxidative Stress in Diabetes Mellitus and Ageing," *Free Rad Biol Med* 10:339–352.

Wynn, J.E. et al. (1970). "The Toxicity and Pharmacodynamics of EGTA: Oral Administration to Rats and Comparisons with EDTA," *Toxicol Appl Pharmacol* 16:807–817.

Yanagisawa, T. et al. "Subacute and chronic toxicity studies of triethylenetetramine dihydrochloride (TJA–250) by oral administration to F–344 rats," *J. Toxicol. Sci.* 23 Suppl. 4:619–642 ( No date Available).

Yücel, D. et al. (1998). "Increased Oxidative Stress in Dilated Cardiomyopathic Heart Failure," *Clin Chem* 44(1):148–154.

* cited by examiner

FRUCTOSAMINE OXIDASE: ANTAGONISTS AND INHIBITORS

CROSS REFERENCE TO RELATED APPLICATIONS

This application is a continuation of U.S. application Ser. No. 09/975,751, filed Oct. 10, 2001, now U.S. Pat. No. 6,610,693 which is a continuation of U.S. application Ser. No. 09/671,967, filed Sep. 27, 2000, now U.S. Pat. No. 6,348,465 which claims priority to PCT/NZ99/00161, filed Sep. 24, 1999; New Zealand application 337042, filed Aug. 9, 1999; New Zealand application 334471, filed Mar. 3, 1999; New Zealand application 332079, filed Sep. 28, 1998; and New Zealand application 332084, filed Sep. 25, 1998, all of which are hereby incorporated by reference in their entirety.

TECHNICAL FIELD

The present invention is in the field of biochemistry. More specifically, the invention involves fructosamine oxidase enzyme inhibitors. Methods of treatment, pharmaceutical compositions, dosage forms, uses of fructosamine oxidase enzyme inhibitors in medicine or for manufacturing pharmaceutical compositions, treatment regimes, and related combinations, methods and products are disclosed herein.

BACKGROUND

Diabetes mellitus is a common disorder affecting nearly 16 million Americans. See, for example, Report of the Expert Committee on the Diagnosis and Classification of Diabetes Mellitus. *Diabetes Care,* 20; 1183–97 (1997). Diabetic individuals are prone to complications which are a major threat to both the quality and the quantity of life. Almost half those diagnosed with diabetes before the age of 31 years die before they reach 50 years largely as a result of cardiovascular or renal complications, often with many years of crippling and debilitating disease beforehand. See, Deckert T., Poulsen J., Larsen M. *Diabetologia* 14:363–70 (1978). It is estimated that diabetic individuals have a 25-fold increase in the risk of blindness, a 20-fold increase in the risk of renal failure, a 20-fold increase in the risk of amputation as a result of gangrene, and a 2- to 6-fold increased risk of coronary heart disease and ischemic brain damage. See, Klein R., Klein B., Moss S., Davis M., DeMets D. *Diabetes Care* 8;311–5 (1985).

Largely because of these long-term complications, the cost of diabetes in the US was estimated as $98 billion in 1997 comprising $44 billion for direct medical costs such as inpatient and outpatient care plus $54 billion for indirect costs such as lost earnings and productivity, and premature death. Medical innovations that can slow the progression of diabetes have tremendous potential to mitigate the associated clinical and cost repercussions See, American Diabetes Association, "Economic consequences of diabetes in the US in 1997," *Diabetes Care* 21:296–309(1998).

Elevated blood glucose levels are now regarded as causative of diabetic complications based on results of the Diabetes Complications and Control Trial (DCCT) and the United Kingdom Prospective Diabetes Study (UKPDS). See, *N Eng J Med.* 379:977–85 (1993) and *Lancet* 352:837–53 (1998). The DCCT and the UKPDS have both demonstrated that the development of complications of diabetes is related with degree of hyperglycemia and that long-term outcome may be ameliorated by rigorous treatment. For example, prognosis is dramatically improved if capillary blood and glycated hemoglobin levels are maintained less than 150 mg/dL and 7.0% respectively.

The mechanism of glucose toxicity in the tissues of patients with diabetes mellitus is unknown. Glucose condenses with free amino groups on structural and functional proteins to form Schiff bases which, in turn, undergo a series of transformations to yield dark-brown Maillard products. It has been proposed that diabetes complications are caused by the non-enzymatic cross-linking of proteins. See, for example, Cerami A., Ulrich P. C., Brownlee M., U.S. Pat. No. 4,758,583 (1988). However, although increased protein cross-linking is seen in the issues of people long-standing diabetes, the role of Maillard products as a causative factor is certainly not clear. See, for example, Wolff S. P., Jiang Z. Y., Hunt J. V. *Free Rad Biol Med* 10;339–52(1991).

Amadori-rearrangement is the most important Maillard transformation because its product, fructosamine, is the precursor of all the browning products. A novel extracellular enzyme which catalyzes the elimination of fructosamines from glycated protein has been isolated. Enzymes which are related have been disclosed. See, for example, Gerhardinger C., et al. *J Biol Chem* 270(1):218–24 (1995); Saxena, A. K. et al., *J Biol Chem* 271(51):32803–9 (1996); and Horiuchi T, et al., *Agric. Biol. Chem.* 53(1):103–110 (1989). Based on its high specificity for glycated protein substrates and its use of oxygen as an acceptor, the enzyme may be classified as fructosamine oxidase 1.5.3. See, Enzyme Nomenclature, Recommendations of the Nomenclature Committee of the International Union of Biochemistry, Academic Press, London pp. 19–22, (1979).

Fructosamine oxidase is a copper metalloenzyme which belongs to the copper amine oxidase group of enzymes which have previously been isolated from bacteria, fungi, yeast, and mammalian sera. Products of the fructosamine oxidase catalyzed reaction are free unglycated protein, α-dicarbonyl sugar, and the active oxygen species superoxide. A highly specific copper chelator, triene, is an irreversible inhibitor of fructosamine oxidase activity. See, for example, Morpurgo L, et al. *Biol Met* 3:114–7 (1990).

Increased fructosamine oxidase activity may cause many of the recognized sequelae of diabetes by degrading fructosamines bound to basement membrane proteins and generating reactive oxygen species as reaction products. For example, superoxide anions cause an increase in intracellular calcium which modulates the activity of nitric oxide synthase. Nitric oxide is a potent vasodilator and it has been implicated in the vascular dysfunction of early diabetes. See, for example, Ido Y., Kilo C., Williamson J. R. *Nephrol Dial Transplant* 11 Suppl 5:72–5 (1996). Reactive oxygen species also cause a drastic dose-dependent decrease in de novo synthesis of heparin sulfate proteoglycans leading to a reduction in anionic sites on the glomerular basement membrane and an increase in basement membrane permeability to cationic plasma proteins such as albumin See, Kashira N., Watanabe Y., Makin H., Wallner E. I., and Kanwar Y. S. *Proc Natl Acad Sci USA* 89:6309–13 (1992). Increased urinary albumin clearance is a risk indicator in people with diabetes mellitus both for evolving renal disease and for early mortality mainly from coronary heart disease. See, for example, Mattock M. B., Barnes D. J., Vibert G. C., et al. *Diabetes* 47:1786–92 (1998).

Once natural antioxidant defenses are exceeded, hydroxyl radicals may be generated from superoxide via a copper catalyzed Haber-Weiss reaction. See, Halliwell B. and Gutteridge J. M. C. "Free radicals in Biology and Medicine" Clarendon Press, Oxford pp. 136–76 (1989). Hydroxyl radicals are extremely reactive species and could cause the permanent site-specific damage to basement membrane proteins and histopathological changes that are typical of diabetic microvascular disease. See, Robbins S. L., Cotran R. S., Kumar V. "Pathologic basis of disease" $3^{rd}$ ed. W. B. Saunders, pp. 991–1061. (1984).

Similarly, any prolonged increase in fructosamine oxidase activity will cause oxidative stress which could account for the excess risk of macrovascular disease and the 75% increase in mortality seen in patients with diabetes mellitus compared with non-diabetic individuals. Recent studies have convincing demonstrated that oxidative modification of low density lipoprotein (LDL) is involved in the development of atherosclerosis of coronary and peripheral arterial vessels and elevated oxidized LDL concentrations are found in subjects with diabetes mellitus. See, Witztum J. L. *Br Heart J* 69 (Suppl):S12–S18 (1993) and Picard S., Talussot C., Serusclat A et al. *Diabetes and Metabolism* 22:25–30 (1996). Oxidative changes to membrane lipids and to membrane protein SH-groups may also cause aberrations in cellular calcium homeostasis and contribute to the increased incidence of cardiac sudden death that is typical of diabetes. See, Yucel D., Aydogdu S., Cehreli S. et al. *Clin Chem* 44:148–54 (1998).

Triethylenetetramine dihydrochloride, also known as trienes or trien-2HCl or trientine dihydrochloride, is a copper chelating agent. Trienes have been used for treating individuals with Wilson's disease. See, for example, Dubois R. S., *Lancet* 2(7676): 775 (1970); Walsh, J. M., *Q J Med.* 42(167): 441–52 (1973); Haslam, R. H., et al., *Dev Pharmacol Ther* 1(5): 318–24 (1980). Trienes have also been used to treat individuals with primary biliary cirrhosis. See, for example, Epstein O., et al., *Gastroenterology* 78(6): 1442–5 (1980). In addition, trienes have been used to inhibit the spontaneous development of hepatitis and hepatic tumors in rats. See, for example, Sone K., et al., *Hepatology* 23(4): 764–70 (1996). Thus far, trienes have not been used in the treatment of diabetes.

All publications and patent cited herein are hereby incorporated by reference in their entirety.

SUMMARY OF THE INVENTION

Excess fructosamine oxidase activity with glycated basement membrane protein substrate plays a vital role in diabetic complications by the formation of α-dicarbonyl and reactive oxygen free radical species.

This damage may be ameliorated by administering specific fructosamine oxidase inhibitors or antagonists selected from the groups: (i) copper chelating agents; (ii) substrate analogues; and (iii) hydrazine compounds.

In one aspect, the present invention consists in a method of treating an individual (human or otherwise) predisposed to and/or suffering from diabetes mellitus with a view to minimizing the consequences of macrovascular and microvascular damage to the patient (e.g., accelerated atherosclerosis, blindness, renal failure, neuropathy, etc.) which comprises, in addition to any treatment in order to control blood glucose levels, at least periodically inhibiting or antagonizing fructosamine oxidase enzyme activity in the patient.

Preferably said inhibition, or antagonism occurs as a result of administration or self-administration of at least one fructosamine oxidase reaction product inhibitor or antagonist.

Preferably any such inhibitor or antagonist is selected from the groups:
 (i) copper chelating agents
 (ii) substrate analogue
 (iii) hydrazine compound Preferably said inhibitor or antagonist is taken orally.

Preferably said inhibitor or antagonist is taken orally as part of a regime, whether totally oral or not, which also involves the control of blood glucose levels.

In a further aspect, the present invention consists in a pharmaceutical composition (preferably oral) suitable for use in such a method, said composition comprising a fructosamine oxidase inhibitor or antagonist in conjunction with a suitable carrier therefor.

In yet a further aspect, the present invention consists in a pharmaceutical composition for reducing macrovascular and microvascular damage in an individual (including a human) suffering from diabetes mellitus, said composition comprising a fructosamine oxidase inhibitor or antagonist and suitable carrier therefor.

Preferably said carrier can be any diluent, excipient or the like and the dosage form of said pharmaceutical composition can be of any appropriate type whether for oral or other administration or self-administration. Long acting release forms are also envisaged within the present invention.

In still a further aspect, the present invention consists in the use of a fructosamine oxidase inhibitor or antagonist in the manufacture of a pharmaceutical composition comprising the fructosamine oxidase inhibitor or antagonist and a suitable pharmaceutical carrier therefor and which composition is useful in treating an individual (human or otherwise) which or who is suffering from diabetes mellitus to reduce macrovascular and microvascular damage (preferably by a method of the present invention).

In still a further aspect, the present invention consists in combination, the treatment regimes, and/or the medicaments of such regimes previously set forth whether packed together or prescribed together or otherwise.

In still another aspect, the invention consists in a method of treating an individual (human or otherwise) predisposed to and/or suffering from diabetes mellitus, which includes inhibiting or antagonizing fructosamine oxidase enzyme activity in the patient with an agent or agents preferably not contraindicated for the patient. Examples of inhibitor or antagonist include but are not limited to those listed hereinafter.

Preferably in one embodiment said agent(s) is or are copper chelating compound(s) administered or self-administered to the patient.

Examples of suitable copper-chelating compounds include triethylenetetramine dihydrochloride (triene), penicillamine, sar, diamsar, ethylenediamine tetraacetic acid, o-phenanthroline, and histidine.

Preferably in another embodiment, said agent(s) is or are substrate analogue compound(s) administered or self-administered to the patient having an amino acid or peptide moiety with a blocked N-terminal amine group.

Examples of a suitable substrate analogue composition are N-acetylcysteine, captopril, lisinopril and enalapril.

Preferably in another embodiment said agent(s) is or are hydrazine compound(s) administered or self-administered to the patient i.e., a compound having a —NHNH$_2$ moiety.

Examples of a suitable hydrazine compound include diaminoguanidine, hydralazine, and carbidopa.

In still another aspect, the invention consists in a dosage regimen for a method of the present invention and/or using dosage units of the present invention.

In still a further aspect, the present invention consists in the use of a pharmaceutical acceptable compounds being at least one of a substrate analogue, a hydrazine compound and a copper chelator in the manufacture of a dosage unit or pharmaceutical composition useful in treating an individual (human or otherwise) which or who is suffering from diabetes mellitus to reduce macrovascular and microvascular damage.

In another aspect, the invention consists in a dosage unit or pharmaceutical composition for an individual useful in a method of the present invention comprising (preferably in effective fructosamine oxidase reaction product inhibiting or antagonizing amounts—separately or collectively) of a compound (or compounds) being a substrate analogue or a hydrazine compound having an —NHNH$_2$ moiety, or both.

Preferably said dosage unit also includes or said pharmaceutical composition also includes one ore more compounds which are a copper chelators.

Preferably said dosage unit or composition is in an oral dosage form optionally with carriers, excipients or, indeed, even other active agents (e.g., means to lower blood glucose levels).

In still another aspect, the invention consists in a regime or dosage unit or pharmaceutical composition for a diabetic or suspected diabetic individual of the copper chelator, triene, providing for the patient a sufficient fructosamine oxidase inhibiting and/or antagonizing effect to reduce macrovascular and microvascular damage.

In still another aspect, the invention consists in a regime or dosage unit or pharmaceutical composition of captopril for a diabetic or suspected diabetic individual, whether effective or intended to be effective in controlling blood pressure of the diabetic patient (at least in part) or not, providing for the patient a sufficient fructosamine oxidase inhibiting and/or antagonizing effect to reduce macrovascular and microvascular damage.

In yet another aspect, the invention consists in a regime or dosage unit or pharmaceutical composition for a diabetic patient or suspected diabetic patient of a hydrazine compound providing for the patient a sufficient fructosamine oxidase inhibiting and/or antagonizing effect to reduce macrovascular and microvascular damage.

In yet another aspect, the invention consists in a regime or dosage unit or pharmaceutical composition for a diabetic patient or suspected diabetic patient of (i) acetylcysteine and
(ii) at lease one other fructosamine oxidase inhibitor and/or antagonist, the mix of (i) and (ii) providing for the patient a sufficient fructosamine oxidase inhibiting and/or antagonizing effect to reduce macrovascular and microvascular damage.

In yet another aspect, the invention consists in a regime or dosage unit or pharmaceutical composition for a diabetic patient or suspected diabetic patient of (i) hydralazine and
(ii) at least one other fructosamine oxidase inhibitor and/or antagonist, the mix of (i) and (ii) providing for the patient a sufficient fructosamine oxidase inhibiting and/or antagonizing effect to reduce macrovascular and microvascular damage.

In still another aspect, the present invention consists in a method of treating an individual human or otherwise) predisposed to and/or suffering from diabetes mellitus which includes inhibiting and/or antagonizing fructosamine oxidase enzyme activity in the patient with acetylcysteine and hydralazine.

In still another aspect, the invention consists in a regime or dosage unit or pharmaceutical composition for a diabetic or suspected diabetic individual which includes acetylcysteine and hydralazine.

In still a further aspect, the present invention consists in the use of co-administration or serial administration of acetylcysteine and hydralazine for the purpose of reducing macrovascular and microvascular damage in an individual.

Preferably said individual is diabetic.

In yet another aspect, the invention consists in a method of treating and/or reducing the likelihood of diabetic cataract in an individual which comprises at least periodically inhibiting and/or antagonizing fructosamine oxidase enzyme activity in the mammal.

Preferably the method involves the administration or self-administration of effective amounts of triethylenetetramine dihydrochloride (triene).

In another aspect, the invention consists in a method of treating and/or reducing the likelihood of diabetic cardiomyopathy in an individual which comprises at least periodically inhibiting and/or antagonizing fructosamine oxidase enzyme activity in the individual.

Preferably the method involves the administration or self-administration of effective amounts of triethylenetetramine dihydrochloride (triene).

Preferably for any of the aforesaid indications triethylenetetramine dihydrochloride (triene) is administered and/or self administered in concert with another (other) fructosamine oxidase enzyme inhibitor(s) and/or antagonist(s).

Preferably said another inhibitor and/or antagonist or said other inhibitors and/or antagonists is or are administered or self administered to elicit a pharmacological effect for another indication yet together with the effect of the triene is or are in an amount or amounts which are effective for treating or ameliorating macrovascular and microvascular damage of such an individual.

Reference is drawn to PCT Application PCT/NZ99/00161, filed Sep. 24, 1999 (claiming priority of New Zealand Patent Specification No. 332085 filed Sep. 25, 1998), the full content of which is hereby incorporated by reference. It discloses methods of monitoring fructosamine oxidase inhibition and/or antagonism of patients, screening and/or determine patients to determine patients at risk to vascular (particularly microvascular) damage and identifying those individuals who will benefit by treatment with fructosamine oxidase inhibitors and/or antagonists, methods of determining fructosamine oxidase levels in a mammal, methods of determining blood plasma fructosamine oxidase levels in a diabetic individual or a suspected individual, methods of assaying blood serum or blood plasma in vitro for fructosamine oxidase, methods of identifying or testing candidate substances and to related methods and procedures.

Preferably the measurement conducted in vitro is of the superoxide reaction product (or any other oxygen free radical product) of fructosamine oxidase.

DETAILED DESCRIPTION OF THE INVENTION

Figure 1:
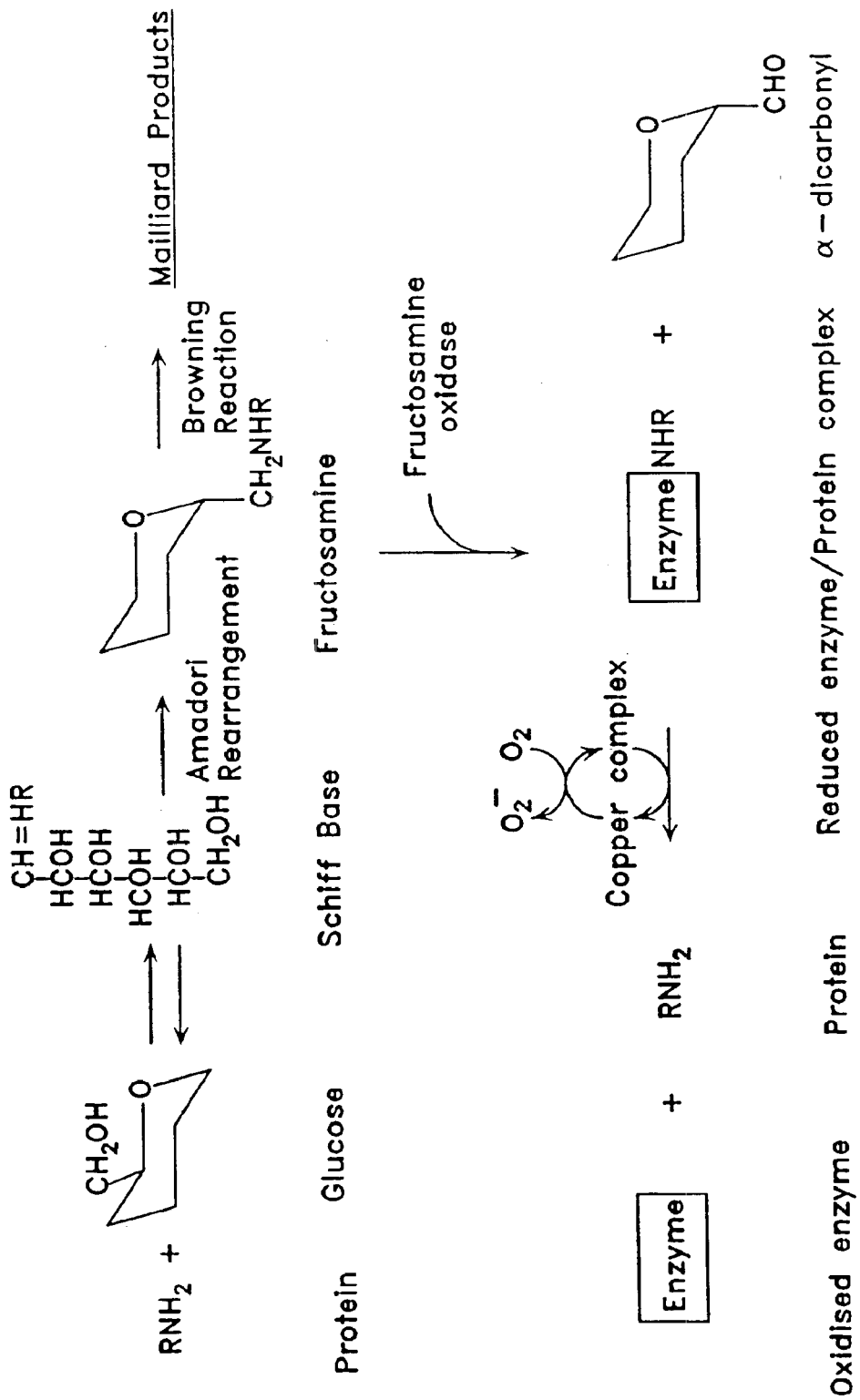
FIG. 1 shows a detailed reaction mechanism for the formation of fructosamine and Maillard products from glucose and protein. Fructosamine oxidase degrades fructosamine by a two-step reaction with initial release of an α-dicarbonyl sugar and subsequent oxidation of the enzyme/protein complex to release free unglycated protein. The reduced copper cofactor is oxidized in vivo by molecular oxygen and the oxidation product is superoxide.

The present invention discloses the use of fructosamine oxidase inhibitors to treat an individual with diabetes mellitus. In one aspect, the invention provides methods of treating diabetes by reducing fructosamine oxidase activity within an individual who is suffering from diabetes.

Definitions

As used herein (including in the claims), the term "inhibitor" is used interchangeably with "antagonist" and refers to a compound which substantially reduces fructosamine oxidase activity.

The term "substantially reduces" refers a reduction of fructosamine oxidase activity by about 5%, more preferably about 10%, even more preferably about 20%, even more preferably about 30%, even more preferably about 40%, even more preferably about 50%, even more preferably about 60%, even more preferably about 70%, even more preferably about 80%, even more preferably about 90%, even more preferably about 100%.

The term "copper chelating agents" means any agent which reduces body fructosamine oxidase activity by lessening the availability of body copper stores and/or by the binding of said copper chelating agent to fructosamine oxidase enzyme. Such binding can have various effects, for example, inactivation of the copper molecule at the reactive center of the enzyme, conformational changes that may affect the activity of the enzyme, or binding a non-reactive portion of the enzyme in a manner that affects the activity of the enzyme Binding can be either reversible or irreversible.

The term "substrate analogue" refers to any chemically modified amino acid or peptide substrate which lessens the activity of fructosamine oxidase enzyme. A non-limiting example by which a substrate analogue can lessen the activity of fructosamine oxidase is by binding to the enzyme. Such binding can have various effects, for example, inactivation of the reactive center of the enzyme, conformational changes that may affect the activity of the enzyme, or binding a non-reactive portion of the enzyme in a manner that affects the activity of the enzyme. Binding can be either reversible or irreversible.

The term "hydrazine compound" means any agent containing the moiety —NH—NH$_2$ which lessens the activity of fructosamine oxidase enzyme. A non-limiting example by which a hydrazine compound can lessen the activity of fructosamine oxidase is by binding to the enzyme. Such binding can have various effects, for example, inactivation of the reactive center of the enzyme, conformational changes that may affect the activity of the enzyme, or binding a non-reactive portion of the enzyme in a manner that affects the activity of the enzyme. Binding can be either reversible or irreversible.

The term "at least periodically" includes from a single administration to continuous administration.

The term "macrovascular damage" refers to accelerated atherosclerosis of large arteries supplying blood to the heart, to the lower limbs, and to the brain. Macrovascular damage can be assessed by various organ imaging techniques such as catheter/dye studies (angiograms) and magnetic resonance angiography. Furthermore, in animal models, whole body responses including, but not limited to, survival and/or weight gain and/or histopathological changes of cardiomyopathy can also be used to assess macrovascular damage. In humans, macrovascular damage can be assessed by any of the measured above as well as monitoring significant physiological changes seen during clinical trial of different fructosamine oxidase inhibitors.

The term "microvascular damage" refers to damage to small arterioles and capillaries, for example, the arterioles and capillaries supplying blood to the retina in the eye, the glomerulus in the kidney, and the peripheral and autonomic nervous system. Microvascular damage of the retina can be assessed by direct ophthalmoscopy, by slit lamp microscopy, or by fluorescein angiography. Microvascular damage elsewhere may be assessed by surrogate measurements. For example, microvascular damage to the kidney glomerulus or peripheral nerves can be assessed by its effect on tissue function, e.g., proteinuria reflects damage to the kidney glomerulus or nerve conduction studies reflect damage to peripheral nerves.

"In concert with" does not necessarily mean as a result of simultaneous administration or self-administration. It can be administered serially and such serial application can be spaced, i.e., triene between meals and another agent with a meal.

The terms "triethylenetetramine dihydrochloride" and "triene" are used interchangeably throughout and includes any pharmaceutically acceptable fructosamine oxidase enzyme inhibiting and/or antagonizing analogue or metabolite thereof (e.g., an acetylated derivative) for the target mammalian species or for a human being capable of administration or self administration in an amount alone or in concert with another fructosamine oxidase enzyme inhibitor and/or antagonist (preferably not contraindicated by toxicity concerns having regard to levels required for effective inhibition and/or antagonism), of providing effective inhibition and/or antagonism.

The term "an effective amount" refers to the amount of one or more fructosamine oxidase inhibitors required to ameliorate the physiological well-being of an individual suffering from diabetes mellitus. This can involve the amount having an effect on fructosamine oxidase activity in an individual to which the inhibitor(s) is being administered.

An "individual" is a vertebrate, preferably a mammal, more preferably a human. Mammals include, but are not limited to, humans and non-rodent pets.

"Comprises" can mean "includes".

"And/or" means both "and" and "or".

Use of Fructosamine Oxidase Inhibitors

Fructosamine oxidase inhibitors can be selected from any number of compounds from several different groups such as copper chelators, substrate analogs, and hydrazine compounds. These compounds are readily available from commercial sources, for example, Sigma Chemical Company (St. Louis, Mo.) or Aldrich Chemicals (Milwaukee, Wis.). Preferably the compound is a triene. The triene can be administered by any appropriate administration route. Non-limiting examples include oral intake (i.e., ingestion by eating or drinking), injection, and mucosal. In one embodiment, triene is administered in a pharmaceutically acceptable composition. In another embodiment, triene is used as pharmaceutically acceptable composition in combination with another compound to lessen fructosamine oxidase activity. Preferably the combination of the triene and a second compound act in cooperation with each other to lower fructosamine oxidase activity. In yet another embodiment, a combination of at least two fructosamine oxidase inhibitors are used in a pharmaceutically acceptable composition. Preferably, the inhibitors do not lessen the efficacy of each other when administered in combination. Preferably, triene is administered with a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in *Remington's Pharmaceutical Sciences*, Alfonso R. Gennaro, ed., 18th edition, (1990). The dosage used is an effective amount of a fructosamine oxidase inhibitor to substantially reduce fructosamine oxidase activity. Preferably, the dosage used is an effective amount of triene to substantially reduce fructosamine oxidase activity. In an alternate embodiment, the dosage use is an effective amount to substantially reduce the symptoms of diabetes and its sequelae (renal dysfuction, visual dysfuction, cardiovascular disease, wound healing problems, etc.). The dosage is preferably about 1 mg/kg to about 1 g/kg, more preferably about 2 mg/kg to about 800 mg/kg, even more preferably about 5 mg/kg to about 600 mg/kg, even more preferably about 7 mg/kg to about 400 mg/kg, even more preferably about 9 mg/kg to about 200 mg/kg, even more preferably about 11 mg/kg to about 100 mg/kg, even more preferably about 13 mg/kg to about 75 mg/kg, even more preferably about 15 mg/kg to about 50 mg/kg, even more preferably about 17 mg/kg to about 35 mg/kg. The administration can be as often as needed to achieve a reduction in fructosamine oxidase activity. A skilled artisan may determine if the combination lessens the efficacy by a stepwise administration of a combination of fructosamine oxidase inhibitors at various dosages and measuring parameters exemplified in the Examples such as weight loss, etc. Fructosamine oxidase inhibitors, preferably triene alone or in combination with other inhibitors, can be administered to individual suffering from diabetes mellitus and its sequelae and/or to individuals who are susceptible to diabetes mellitus (i.e., genetic predisposition). Genetic pre-disposition can be determined by examination and analysis of family history of diabetes mellitus or by genetic markers correlated with development of diabetes mellitus.

EXAMPLES

Example 1

Extraction of Holoenzyme

Fructosamine oxidase in blood plasma is largely found as an enzyme-substrate conjugate, bound to peptides and proteins (FIG. 1). To obtain a maximal yield of active holenzyme, it was necessary to make the pH of the media alkaline preferably with phosphate buffer, to add sulphydryl reagents, and to incubate the mixture with pro-oxidant so that glycated species were released. Most effective activation was found with cupric salts.

Fructosamine oxidase holenzyme was separated from inactive apoenzyme by affinity adsorption chromatography. A suitable glycated affinity support was prepared from alkylamine beads or beaded cross-linked agarose with amino terminal residues by 6–10 atom spacer arms (available from Pierce™, Bio-Rad™, and Pharmacia™). Affinity support was glycated by incubating with 400 mM potassium phosphate buffer pH 7.4 containing 50 mM glucose and 0.01% sodium azide at 37° C. for 7 days. Holoenzyme bound tightly to glycated amino residues and residual copper was readily removed by washing with water. Active holoenzyme was eluted with 800 mM NaCl in 50 mM sodium acetate buffer pH 4.8. Active fractions were pooled and protein was precipitated with 50% cold acetone solvent The protein pellet was reconstituted with a minimal volume of water or physiological saline and lyophilized for long term storage.

Figure 2:
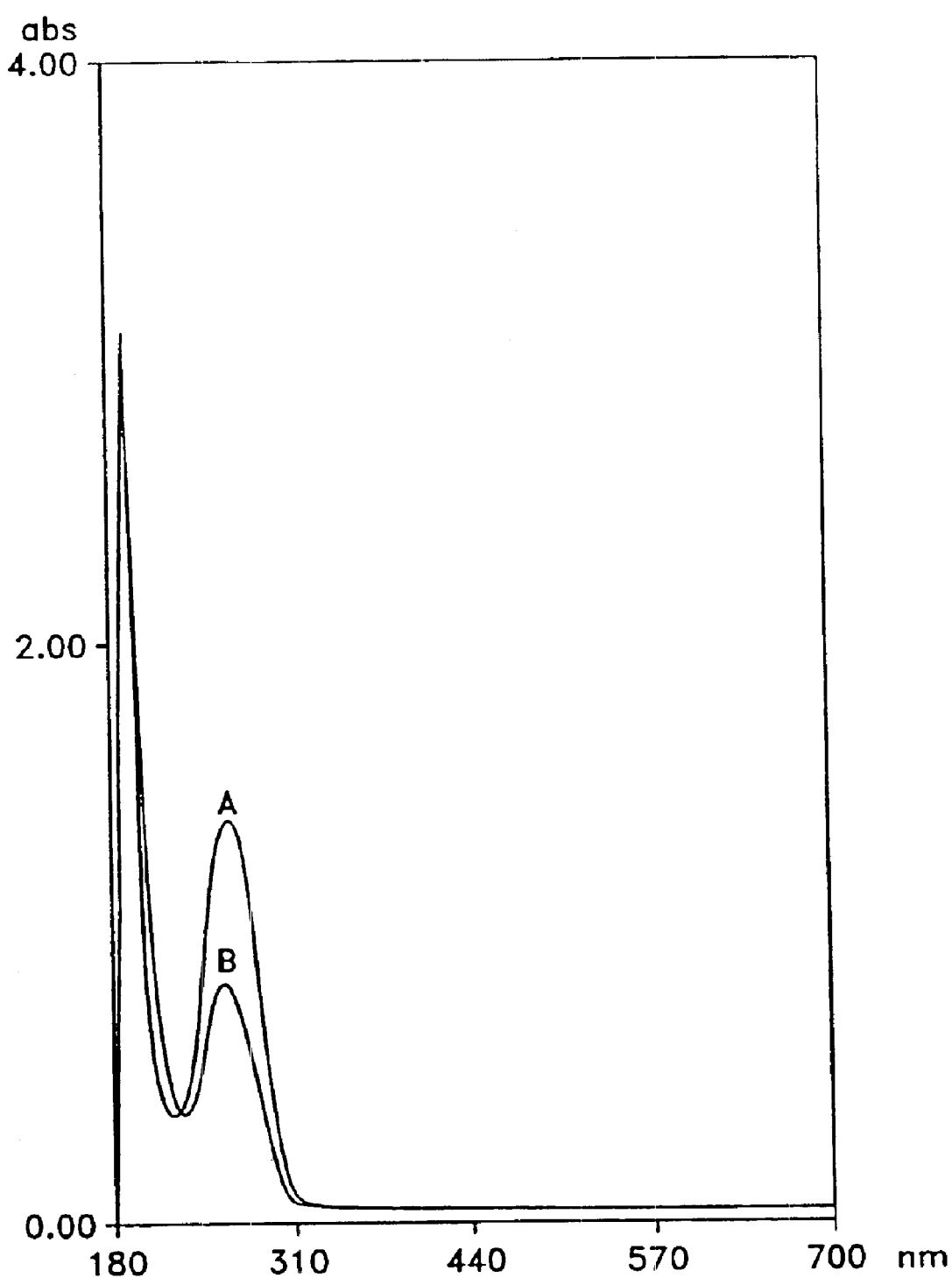
FIG. 2 shows absorbance spectra of the fructosamine oxidase enzymes extracted from pooled human sera (A) and from the microbial organism, *Enterbacter aerogenes* (B).
Figure 3:
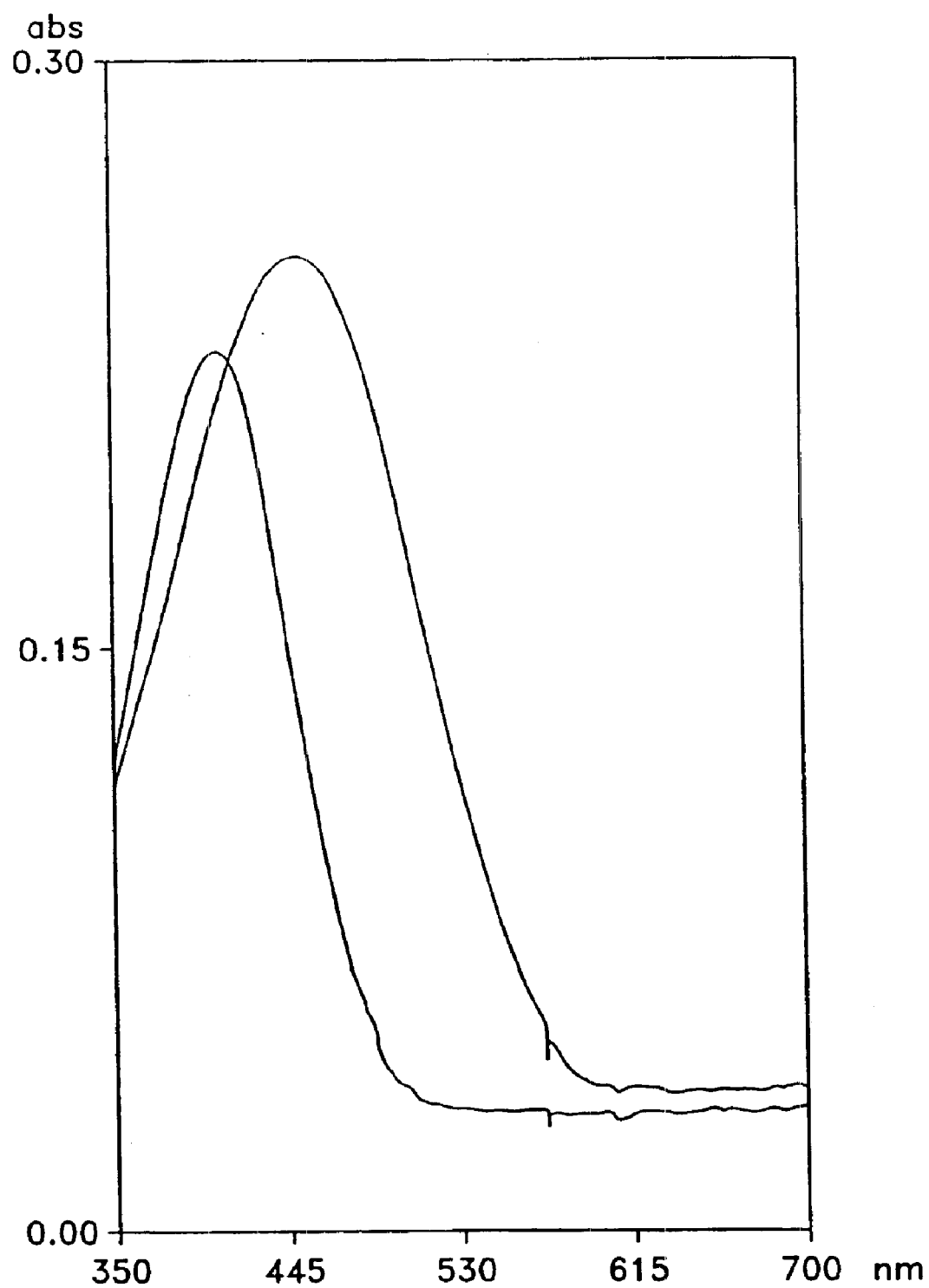
FIG. 3 shows spectra of p-nitrophenylhydrazine (NPH) adduct of the *Enterbacter aerogenes* enzyme (A) and a red absorbance shift when the NPH-enzyme adduct is diluted in 2M KOH.

Extraction of 35 mL pooled diabetic and non-diabetic human sera yielded a clear colorless preparation with absorbance peaks at 196 nm and 264 nm typical of the absorbance spectra of fructosamine oxidase (FIG. 2). A fructosamine oxidase enzyme from *Enterobacter aerogenes* showing absorbance peaks at 196 nm and 255 nm was included for comparison. Enzyme activity and relative activity was as follows.

TABLE 1

| Sample | Protein (μg/mL) | Cytochrome c activity*(U/L) | Sp activity† (U/g) |
|---|---|---|---|
| human | 32.9 | 4.58 | 139.4 |
| E aerogenes | 541.5 | 66.32 | 115.11 |

*Enzyme extract was preincubated in 0.05 M TES buffer pH 7.4 containing 1 mM DMF substrate at 37° C. for 5 minutes. Enzyme activity was measured with 10 μM ferricytochrome c. The reaction was started with 50 μM fructosamine substrate as g-BSA and $\Delta A_{550nm}$ was determined over 5 minutes.
†Protein concentration determined from $A_{210nm}$–$A_{220nm}$ compared with BSA standards.

Cofactor Identification

The p-nitrophenylhydrazine (NPH) adduct of *Enterbacter aerogenes* enzyme with $A_{max}$ 399 nm was obtained as described previously. See, Palcic M. M., lanes S. M. *Meth Enzymol* 258:34–8 (1995). A red absorbance shift to $A_{max}$ 438 nm was observed when the NPH-enzyme adduct was diluted in 2M KOH. Such an absorbance shift was typical of the quinone cofactors of copper amine oxidase.

Example 2

Identifying Fructosamine Oxidase Inhibitors

The purpose of this example was to demonstrate how the fructosamine oxidase assay, the subject of a PCT International patent specification NZ 332085 the contents of which are hereby incorporated by reference, may be used in identifying and grading candidate fructosamine oxidase inhibitors. This approach took into account the activity of the drug in a human plasma matrix in vitro. Enzyme inhibitors have wide and numerous applications in clinical medicine as treatments for a range of metabolic disorders. For example, angiotensin converting enzyme inhibitors have been used in the treatment of hypertension. See, for example, Harris E. E., Patchett A. A., Tristram E. W., and Wyvratt M. J., "Aminoacid derivatives as antihypertensives" U.S. Pat. No. 4,374,829 (1983). Similarly, 3-hydroxy-3-methylglutaryl-coenzyme A (HMG-CoA) reductase enzyme inhibitors have been used in the treatment of hypercholesterolemia. See, for example, Hoffman W. F., Smith R. L., Lee T. J., "Novel HMG-CoA reductase inhibitors" U.S. Pat. No. 4,866,090 (1989). Fructosamine oxidase inhibitors may be selected from those substances which bind and block the quinone co-factor (hydrazine compounds), the copper co-factor (copper chelators), or which mimic the normal substrate of the enzyme (substrate analogue).

Method:

Potential fructosamine oxidase inhibitors were tested on human serum or plasma (individually and in combination) using the method of assaying fructosamine oxidase activity described in detail in a New Zealand Patent Specification No. 332085. Irreversible enzyme inhibition was characterized by a progressive decrease in activity with time ultimately reaching complete inhibition even with very dilute inhibitor concentrations provided that the inhibitor is in excess of the amount of enzyme present.

Results:

The relative activity of a selection of hydrazine, copper chelator, and substrate analogue Fructosamine oxidase inhibitors are shown in Table 2. In some instances, there was a degree of overlap between classes, i.e., some hydrazine compounds were also copper chelators. To clarify this point, copper chelating potential for some compounds is indicated (β). The effectiveness of the inhibitor was expressed not by an equilibrium constant but by a velocity constant (K) which determined the fraction of the enzyme inhibited in a given period of time by a certain concentration of inhibitor. The specificity of the inhibitor for the active center of the enzyme was indicated by the concentration of inhibitor causing 50% inactivation of the enzyme ($IC_{50}$).

TABLE 2

| | $IC_{50}{}^1$ | $K(min^{-1})^2$ | $β^3$ |
|---|---|---|---|
| Inhibitor: Hydrazine compounds | | | |
| aminoguanidine | 231. μM | 0.0067* | – |
| semicarbazide | 45. μM | 0.0276* | +++ |
| benserazide | 13.6 μM | 0.0095* | |
| oxalic dihydrazide | 1.59 μM | 0.0542 | – |
| hydralazine | 1.52 μM | 0.0029 | +++ |
| phenylhydrazine | 0.81 μM | 0.1160 | – |
| carbidopa | 0.50 μM | 0.1496 | |
| diaminoguanidine | 0.36 μM | 0.1340 | – |
| Inhibitor: Substrate analogues | | | |
| lisinopril | 216.9 μM | 0.0174 | |
| enalapril | 3.95 μM | 0.0326 | +++ |
| captopril | 1.78 μM | 0.0259 | – |
| acetylpenicillamine | 1.06 μM | 0.0811 | |
| acetylcysteine | 0.83 μM | 0.1677 | |
| Inhibitor: Copper chelators | | | |
| desferrioxamine | 40.6 μM | 0.0109* | |
| EDTA | 15.7 μM | 0.0755* | |
| Sodium azide | 9.48 μM | 0.0004 | |
| Potassium cyanide | 6.36 μM | 0.0116 | |
| triene | 5.40 μM | 0.0196 | |
| o-phenanthroline | 4.25 μM | 0.0385 | |
| histidine | 2.29 μM | 0.0554 | |
| Inhibitor: Combined agents | | | |
| acetylcysteine + hydralazine | 0.57 μM | 0.1654 | |
| acetylcysteine + diaminoguanidine | 1.07 μM | 0.0795 | |
| acetylcysteine + histidine | 1.11 μM | 0.0722 | |
| acetylcysteine + carbidopa | 0.27 μM | 0.2000 | |

[1] fresh human sera was incubated with 0–1,000 μM inhibitor in 0.05 M TES buffer pH 7.4 at 37° C. for 5 minutes. Enzyme activity was measured with 10 μM ferricytochrome c. The reaction was started with 50 μM fructosamine substrate as g-BSA and $\Delta A_{550nm}$ was determined over 5 minutes.
[2] rate constants were calculated from the reaction of fructosamine oxidase either with 1.0 μM inhibitor or with 10.0 μM inhibitor (*).
[3] copper chelating potential (β) was determined from ability of agent to remove copper under dialysis from copper-saturated BSA substrate.

Conclusions:

Irreversible inhibition of fructosamine oxidase is feasible.

Inhibitors may be broadly categorized in three classes of compound: hydrazines; substrate analogues; and copper chelators.

Fructosamine oxidase activity in human blood plasma may be eliminated by micromolar concentrations of inhibitors.

Many of the active inhibitors are drugs which have already been administered as medicines in humans to treat other disorders (not diabetes).

Example 3

Clinical Utility of Fructosamine Oxidase Inhibition: First Preclinical Study

The purpose of this example was to demonstrate how the clinical usefulness of candidate fructosamine oxidase inhibitors may be assessed using a standard animal model of diabetes mellitus, the steptozocin-diabetic rat (STZ rat). This approach took into account drug bioavailability, the activity of the drug and its metabolites, and any drug adverse effects or toxicity factors.

Method:

48 Wistar rats aged 6–8 weeks and weighing 200–300 g were randomized:

Group 1 Non-diabetic control
Group 2 Diabetic control
Group 3 Diabetic treated with hydralazine
Group 4 Diabetic treated with EDTA
Group 5 Diabetic treated with hydralazine and acetylcysteine
Group 6 Diabetic treated with acetylcysteine Streptozotocin (60 mg per kg) was administered into a lateral tail vein.

Non-diabetic controls received a sham injection of buffer. Diabetes was confirmed by venous blood glucose measurement >15 mmol/L after 1 week and diabetic animals were treated with subcutaneous injections of ultralente insulin (4 U/injection) 3–5 days per week to maintain body growth. Medications were administered 50 mg/L in the drinking water over an 8 month period. Timed urine collections and venous plasma samples were obtained at monthly intervals.

Results:

Blood glucose control: Rate of conversion to diabetes with intravenous STZ administration was >95%. Intravenous STZ induced a severe form of insulin-dependent diabetes which was sustained over the entire 8 month duration of the study. Despite insulin replacement therapy, glycemia control was poor as evidenced by mean±SD glucose (week 4) and $HbA_{1c}$ (week 32) levels in Table 3.

TABLE 4

| | Group 1 | Group 2 | Group 3 | Group 4 | Group 5 | Group 6 |
|---|---|---|---|---|---|---|
| Survivors at week 32 | 8 | 2 | 6 | 5 | 8 | 7 |
| Significance* | — | — | ns | ns | P < 0.025 | P < 0.05 |

*Chi-square test compared with untreated STZ rats (Group 2)

Figure 4:
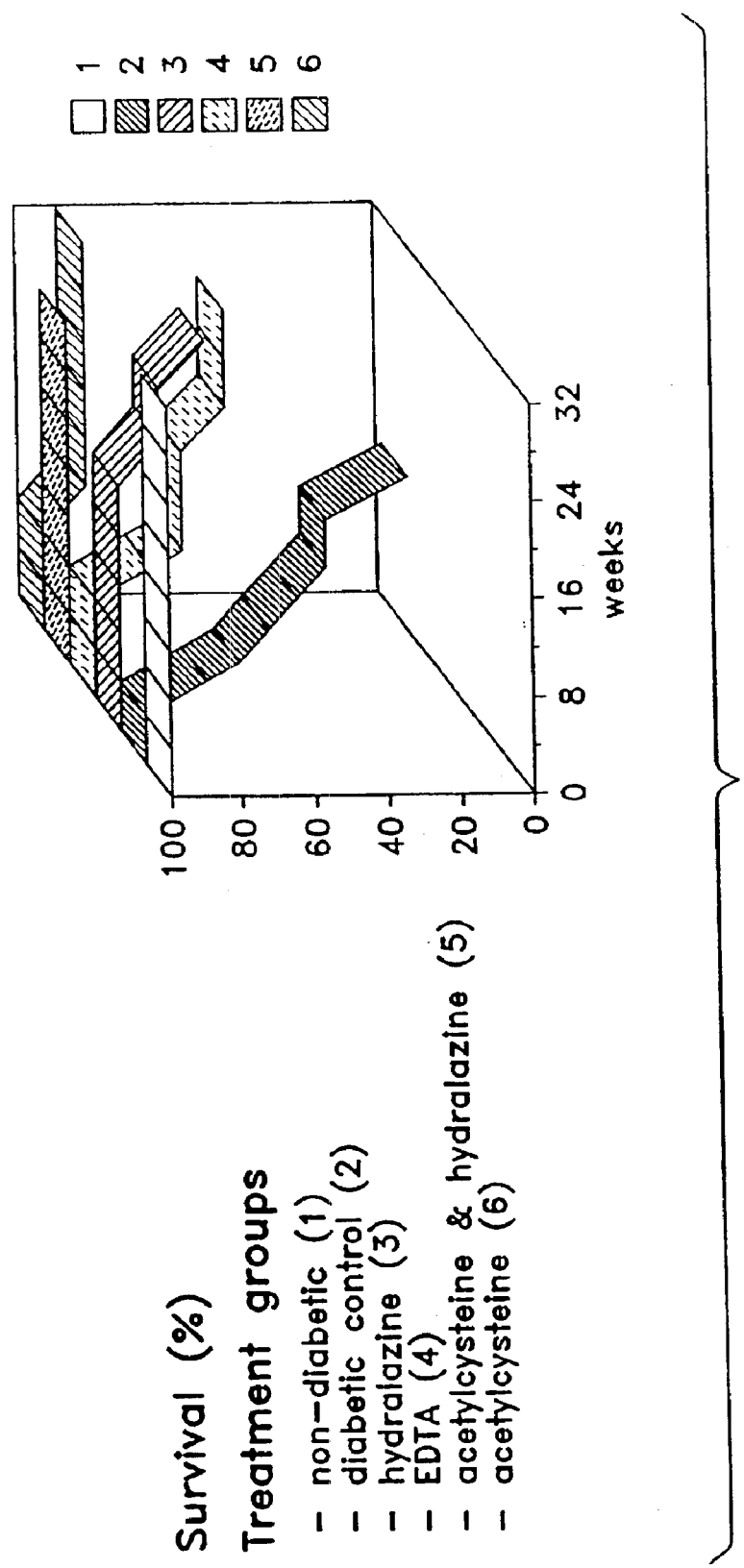
FIG. 4 shows survival curve for non-treated STZ-diabetic rats compared with diabetic animals treated with fructosamine oxidase inhibitors.

The survival curve for STZ rats compared with non-diabetic controls is shown in FIG. 4. Death was presumed secondary to a cardiovascular event. In general, renal function remained normal.

Figure 5:
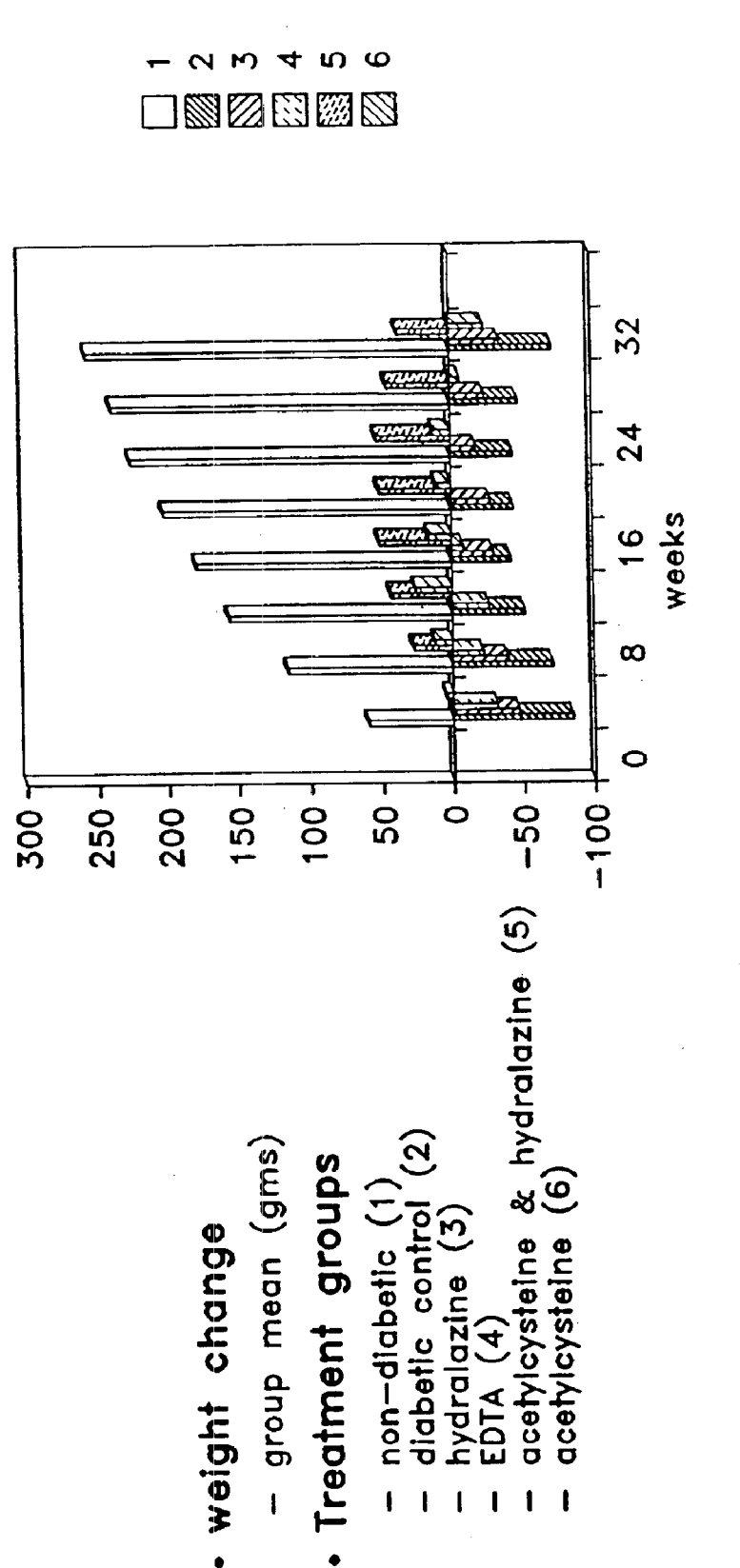
FIG. 5 shows monthly growth of treated and untreated STZ-diabetic rats compared with non-diabetic animals.

(c) Weight gain: There was a progressive weight gain amongst non-diabetic controls over the 32 weeks of the study which was abolished in the STZ diabetic animals. At the end of the 32 week study period, mean weight change amongst surviving study animals was: Group 1, +74.6%; Group 2, −21.0%, Group 3, −11.0%; Group 4, +1.2%, Group 5, +16.0%; and Group 6, −8.1% (FIG. 5). Compared with untreated diabetic controls, fructosamine oxidase inhibitors caused an improvement in weight gain roughly in proportion to the activity of the inhibitor (Table 2), i.e., acetylcysteine/hydralazine-22 EDTA>acetylcysteine>hydralazine.

(d) Clinical pharmacokinetics:

Hydralazine

The bioavailability of hydralazine in man after oral administration is 26–55%. However, only 2.0–3.6% of the drug is excreted in the urine unchanged over 24 hours after oral administration. Most of the drug is recovered as an inactive acetylated product See, Talseth T., *Eur J Clin Pharmacol* 10:395–401 (1976) and Talseth T., *Clin Pharmacol Ther* 21:715–20 (1977). This could account for the reduced efficacy of hydralazine as a fructosamine oxidase inhibitor in the current study. Furthermore, drug doses administered to each STZ rat were calculated as 12.5 mg hydralazine/day or 35 mg/kg, based on an average consumption 250 mL water per day and assuming a mean body mass of 350 g. This rat dose far exceeds the maximum recommended human dose of 200 mg hydralazine per day (3 mg/kg assuming a mean body mass 70 kg).

EDTA

The bioavailability of EDTA after oral administration is very low (less than 5%) because of poor absorption from the gut limiting its usefulness in humans to parenteral administration or irrigation techniques. See, for example, Wynn J. E. et al. *Toxicol Appl Pharmacol* 16:807–17(1970).

TABLE 3

| | Group 1 | Group 2 | Group 3 | Group 4 | Group 5 | Group 6 |
|---|---|---|---|---|---|---|
| Glucose (mmol/L) | 9.1 ± 1.5 | 30.1 ± 9.7 | 35.7 ± 9.5 | 39.0 ± 6.4 | 30.4 ± 8.8 | 37.8 ± 5.2 |
| $HbA_{1c}$ (%) | 3.92 ± 0.11 | 10.85 ± 0.05 | 8.65 ± 1.18 | 9.30 ± 0.63 | 8.72 ± 0.55 | 9.47 ± 1.23 |

(b) Survival: Mortality rate amongst untreated STZ rats was extremely high. Survival was improved significantly by the administration of fructosamine oxidase inhibitors (Table 4).

Acetylcysteine

Acetylcysteine is rapidly absorbed from the gut with an bioavailability in man varying between 6 and 10%. See, for example, Borgstrom L. et al. *Eur J Clin Pharmacol* 31:217–22 (1986). However, the drug is rapidly degraded in the liver by elimination of the acetyl moiety. See, for example, Holdiness M. R., *Clin Pharmacokinet* 20:123–34 (1991). Induction of liver enzymes could account for the progressive loss of drug efficacy seen after week 12 in the current study.

Conclusions:

Streptozocin induces a severe form of Type I diabetes in the rat with a high morbidity and mortality.

Survival of STZ rats was enhanced by treating with fructosamine oxidase inhibitors in proportion to their activity in an in vitro assay.

Weight gain of STZ rats was enhanced by treating with fructosamine oxidase inhibitors.

There was some benefit in co-administering acetylcysteine and hydralazine suggesting a synergy effect between classes of fructosamine oxidase inhibitors.

Based on these in vivo studies in the rat, the efficacy of a candidate of fructosamine oxidase inhibitor in a human is likely to be influenced by bioavailability of the drug, degradation of the active compound in vivo, and maximum oral tolerated dose of the drug.

Example 4

Clinical Utility of Fructosamine Oxidase Inhibition: Second Preclinical Study

The purpose of this example was to demonstrate how the clinical usefulness of candidate fructosamine oxidase inhibitors, alone and in combination, may be assessed using a standard animal model of diabetes mellitus, the streptozocin-diabetic rat (STZ rat). This approach took into account drug bioavailability, the activity of the drugs and their metabolites, interactions between drugs, and any drug adverse effects or toxicity factors.

Method:

80 Wistar rats weighing 200–300 g and aged of 6–8 weeks were randomized:

Group 1 Nondiabetic control
Group 2 Diabetic control
Group 3 Diabetic treated with captopril (substrate analogue)
Group 4 Diabetic treated with carbidopa (hydrazine)
Group 5 Diabetic treated with triene (copper chelator)
Group 6 Diabetic treated with captopril and triene
Group 7 Diabetic treated with captopril and carbidopa
Group 8 Diabetic treated with triene and carbidopa Diabetes was induced by administering streptozotocin (60 mg per kg) by intraperitoneal injection. Nondiabetic controls received a sham injection of buffer. Diabetes was confirmed by venous blood glucose measurement >15 mmol/L after 1 week and diabetic animals were treated with subcutaneous injections of ultralente insulin (4 U/injection) 3 days per week to maintain body growth. Medications were administered at a concentration of 50 mg/L in the drinking water over an 6 month period. Timed urine collections and venous plasma samples were obtained at monthly intervals. Animals were monitored for blood glucose control and survival rate over the course of study. Animals were sacrificed and subjected to post-mortem examination at the end of the study to determine various parameters of fructosamine oxidase activity inhibitor efficacy. Parameters include, but are not limited to, survival rate, weight gain, cataract formation, and cardiomyopathy.

Results:

Blood glucose control: Rate of conversion to diabetes with intraperitoneal STZ administration was ≈80%. Poor glycemic control was sustained over the 6 month duration of the study as evidenced by mean±SD $HbA_{1c}$ (week 4, 12, and 24) levels (Table 5).

TABLE 5

| $HbA_{1c}$ | Group 1 | Group 2 | Group 3 | Group 4 | Group 5 | Group 6 | Group 7 | Group 8 |
| --- | --- | --- | --- | --- | --- | --- | --- | --- |
| Week 4 | 4.1 ± 0.1 | 8.3 ± 0.1 | 8.5 ± 0.9 | 9.0 ± 1.0 | 8.0 ± 1.0 | 9.0 ± 5.2 | 9.1 ± 1.5 | 9.1 ± 1.5 |
| Week 12 | 4.1 ± 0.1 | 9.2 ± 0.6 | 9.2 ± 1.1 | 9.6 ± 0.7 | 8.8 ± 0.9 | 9.5 ± 0.8 | 9.5 ± 1.0 | 9.3 ± 0.9 |
| Week 24 | 3.7 ± 0.1 | 9.4 ± 01.3 | 9.6 ± 1.3 | 9.9 ± 1.1 | 9.0 ± 1.4 | 9.5 ± 1.3 | 9.8 ± 1.2 | 9.1 ± 1.2 |

(b) Survival: Compared with intravenous administration of STZ, intraperitoneal administration of STZ induced a less severe form of diabetes with lesser mortality rate. At the end of the 24 week study period, mortality rate amongst study animals was: Group 1, 0%; Group 2, 14.3%, Group 3, 0%; Group 4, 0%, Group 5, 0%; Group 6, 12.5%, Group 7, 0%, and Group 6, 0%. There was no significant difference between groups because of the low frequency of events.

(c) Weight gain: STZ diabetes caused a profound weight loss in diabetic rats compared with non-diabetic controls. Mean weight gain of study animals from the beginning to the end of the 24 week period are indicated in Table 6.

TABLE 6

| | Group 1 | Group 2 | Group 3 | Group 4 | Group 5 | Group 6 | Group 7 | Group 8 |
| --- | --- | --- | --- | --- | --- | --- | --- | --- |
| Mean ± SEM weight gain | 342.8 ± 13.7 | 54.4 ± 12.5 | 60.7 ± 20.7 | 33.7 ± 20.4 | 123.6 ± 20.5 | 56.1 ± 21.3 | 55.1 ± 17.1 | 75.8 ± 25.4 |
| P* | — | ns | ns | ns | 0.0138 | ns | ns | ns |

*Student's t test compared with untreated STZ rats (Group 2)

Triene administered alone (Group 5) caused a significant improvement on weight gain compared with untreated STZ diabetic control rat group (Group 2). There was no evidence of synergy between classes of fructosamine oxidase inhibitors.

Cataract formation: Cataract has been a recognized long-term complication of poorly controlled diabetes. Gross cataract formation in STZ rats compared with diabetic control animals by the end of the study at week 24 is shown in Table 7.

TABLE 7

|  | Group 1 | Group 2 | Group 3 | Group 4 | Group 5 | Group 6 | Group 7 | Group 8 |
| --- | --- | --- | --- | --- | --- | --- | --- | --- |
| No (%) with cataract | 0 (0%) | 8 (40%) | 2 (25%) | 2 (25%) | 0 (0%) | 2 (28%) | 5 (62%) | 1 (12%) |
| P* | — | — | ns | ns | <0.10 | ns | ns | ns |

*Chi-square test compared with diabetic control rats (Group 2)

Although not significant at the P=0.05 level, triene appeared more effective than captopril and carbidopa in inhibiting gross cataract formation There was no evidence of synergy between classes of fructosamine oxidase inhibitors.

(e) Diabetic cardiomyopathy Cardiomyopathy has been a recognized long-term complication of poorly controlled diabetes. Macroscopically, hearts of STZ rats were dilated with thing of the ventricular wall. Sections stained with hematoxylin and eosin and Masson's Trichrome showed focal pallor with a loss of normal architecture in the myocardium of both ventricles that began at the sub-endocardial and sub-epicardial regions and spread to encompass the whole ventricular wall in severely affected animals. There was also marked infiltration by fibrous connective tissue between myocytes and increased fibrous connective tissue in the walls of intramural arteries. These appearance were consistent with dilated cardiomyopathy. Gross myocardial fibrosis in STZ rats compared with non-diabetic control animals by the end of the study at week 24 is shown in Table 8.

TABLE 8

|  | Group 1 | Group 2 | Group 3 | Group 4 | Group 5 | Group 6 | Group 7 | Group 8 |
| --- | --- | --- | --- | --- | --- | --- | --- | --- |
| No (%) rats with severe fibrosis | 0 | 10 | 6 | 2 | 0 | 6 | 8 | 7 |
| P | — | — | ns | ns | <0.005 | ns | <0.005 | ns |

*Chi-square test compared with diabetic control rats (Group 2)

Triene appeared to be highly effective in inhibiting the development of diabetic cardiomyopathy. Diabetic cardiomyopathy causes histopathological and functional changes in the heart The disease can be assessed post-mortem by examining the histology. Alternatively, the disease can be assessed ante-mortem by measuring heart function using echocardiography, cardiac catheter studies, or magnetic resonance imaging of the heart. There was no evidence of synergy between classes of fructosamine oxidase inhibitors.

(f) Clinical pharmacokinetics:

Triene The bioavailability of triene was less than 10%. Bioavailability refers to the degree to which a drug or other substance becomes available to the target tissue after administration. Bioavailability is usually expressed as that proportion of an administered dose that may be measured in the blood stream. See, for example, Kodama H. et al., *Life Sci* 61:899–907 (1997). Most of the unchanged drug was cleared in the urine within the first 6 hours of oral dosing mainly as an acetyl derivative indicating that a three or four times daily drug regimen or a sustained release preparation was required. See, for example, Kodama H. et al. supra. In addition, plasma levels in non-fasted rats was significantly lower than those observed in fasted animals and the uptake of triene from the intestinal brush border was competitively inhibited by other amine compounds. See, for example, Tanabe R. et al. *J Pharm Pharmacol* 48:517–21 (1996). This implied that triene was best administered in the fasting state. Fasting state was usually about half an hour before meals. Interference in the absorption of drug from the intestinal brush border could account for discrepancies between triene treatment groups (Groups 5, 6, and 8). Finally, in the current study lasting approximately 6 months, each STZ rat consumed approximately 250 mL water per day (12.5 mg triene/rat/day). Assuming a mean body mass of 350 g, this dose of triene equated to 35 mg/kg. The dose of triene previously used in treating humans with another non-diabetic condition ranged between 1.2–2.4 g (17–35 mg/kg assuming a mean body mass 70 kg). See, Walshe J. M. *Lancet* 8273:643–7 (1982). This implied that humans may be safely treated with comparable doses of trienes to those administered to rats in the current study to thereby elicit the fructosamine oxidase inhibition and/or antagonism advantages in a diabetic patient referred to herein.

Captopril The bioavailability of captopril was approximately 65% after an oral dose. However, the drug was almost completely bound in vivo to albumin and other plasma proteins and formed inactive mixed disulfides with endogenous thiols so that plasma levels of active drug might have been very low. The elimination half life of unchanged captopril was approximately 2 hours. See, Duchin K. L. et al. *Clin Pharmacokinet* 14:241–59 (1988). These observations might explain the reduced efficacy of captopril in the STZ rat compared with in vitro studies. Furthermore, each STZ rat consumed approximately 12.5 mg captopril/day which equated to 35 mg/kg assuming a mean body mass of 350 g. This dose far exceeded the maximum recommended human dose of 150 mg captopril per day (2 mg/kg assuming a mean body mass of 70 kg).

Carbidopa In a study of beagle dogs, the oral absorption of carbidopa was almost complete and the absolute bioavailability was 88%. The biological half-life was 5 hours. See, for example, Obach R et al. *J Pharm Pharmacol* 36:415–6 (1984). However, carbidopa was an unstable compound and it degraded naturally in a short period. Solutions left to stand exposed to light at room temperature will undergo 50% oxidative degradation in 24 hours. See, for example, Pappert E. J. et al. *Movement Disorders* 12:608–23 (1997). Reduced bioavailability due to oxidative degradation of the active drug both prior to its consumption and post-ingestion in the rat could explain (in part) the reduced efficacy of carbidopa in the current study. Finally, each STZ rat consumed approximately 12.5 mg carbidopa/day which equated to 35 mg/kg assuming a mean body mass of 350 g. This dose far exceeded the maximum recommended human dose of 200 mg carbidopa per day (3 mg/kg assuming a mean body mass of 70 kg).

Conclusions:

Intraperitoneal streptozocin was associated with a lower mortality rate than intravenous streptozocin in the rat.

Weight gain over a 6 month period was enhanced in STZ rats treated with the copper chelator triene, as shown in Table 6. Captopril and carbidopa were ineffective.

Cataract development may be inhibited by triene. Efficacy of triene was diminished when the drug was co-administered with either captopril or carbidopa.

The development of diabetic cardiomyopathy was prevented by treatment with triene. Triene was administered in the amount of 50 mg of drug per liter in the drinking water. This amount resulted in an average dose of 12.5 mg triene per rat per day based on an estimated water intake of 250 mL per day. In rat groups 6 and 8, triene was mixed with captopril and carbidopa, respectively, in the drinking water. Concentrations of triene, captopril, and carbidopa were all 50 mg drug per liter drinking water.

Efficacy of triene was diminished when the drug was co-administered with either captopril or carbidopa (50 mg drug per liter drinking water).

Oral doses of triene which inhibited the development of complications in the rat (cataract, cardiomyopathy, and early death) were equivalent on a body mass basis to doses of triene which had previously been used to treat human beings with another condition (not diabetes).

When administered to humans on a three or four times daily basis or as a sustained release preparation in previously tolerated doses 1.2–2.4 g/day, triene may provide an effective means of treating the long-term complications of diabetes mellitus.

Example 5

Clinical Utility of Fructosamine Oxidase Inhibition: Double-Blind, Placebo-Controlled Clinical Trial The purpose of this example is to demonstrate how the clinical usefulness of candidate fructosamine oxidase inhibitors is to be assessed in diabetic human subjects. A detailed protocol based on this proposal has been approved by the Auckland Regional Ethics Committee. This approach takes into account drug bioavailability, the activity of the drugs and their metabolites, interactions between drugs, any drug adverse effects or Toxicity factors and the "scale-up" factor from rat to human treatment.

Objective: A pilot study to determine whether triene reduces the rate of progression of renal disease and associated microvascular complications in patients with diabetic nephropathy due to Type II diabetes mellitus.

Patient population: 60 men and women aged between 40 years and 70 yeas of age with poor blood glucose control and diabetic nephropathy due to Type II diabetes mellitus. Poor blood glucose control was defined as a hemoglobin $A_{1c}$ ($HbA_{1c}$) greater than 7% in this group of patients with advanced microvascular complications, i.e., diabetic nephropathy. Diabetic nephropathy is a clinical syndrome defined as the patient having: (i) albuminuria greeter than 300 mg per liter; (ii) plasma creatinine greater than 150 $\mu$mol per liter; and (iii) some evidence of diabetic retinopathy.

Study design and duration: Randomized double-blind, placebo-controlled study design consisting of five periods:
  screening period (detecting possible candidates who meet study criteria);
  enrolment period (securing informed consent and baseline ments);
  run-in period (trial of acceptability of study protocols and study medication);
  maintenance period (treatment with drug/placebo, monitoring efficacy/safety);
  follow-up period (detect any untoward effect when medication is discontinued).

Blinded therapy (triene 400 mg or placebo) is administered three time daily ½ hour before meals in addition to current anti-hypertensive and hypoglycemic therapies. The study terminates when all patients are randomized and have been in the study (maintenance period) for a minimum of 6 months. All randomized patients who discontinue study drug for any reason other than death are followed for the entire duration of the study; patients who undergo renal transplantation or dialysis are followed for vital status only.

Outcomes Efficacy:
  The primary outcome measure consists of rate of decline in renal function as measured by glomerular filtration rate (creatinine clearance). Creatinine clearance is a standard means of measuring renal function (glomerular filtration rate) in human subjects and since this procedure is a standard method and routine to a person of skill in arts, no further definition or explanation is necessary.
  The secondary outcome measures to be evaluated are development of diabetic retinopathy, diabetic peripheral neuropathy, and diabetic autonomic neuropathy.

Safety:
Safety parameters evaluated are adverse events and clinical laboratory abnormalities. Adverse events can be categorized as serious (i.e., life-threatening) or non-serious. Non-serious adverse events are any events, which the clinical investigator may consider to be secondary to the administration of the drug Non-limiting examples include headache, nausea, cough, diarrhea, weight loss, alopecia, and impotence. Clinical laboratory abnormalities are assessed at time points by medical history, physical examination, and laboratory analyses and compared between groups. Non-limiting examples include anemia, thrombocytopenia, leukopenia, iron deficiency, disordered liver function tests, and impaired renal function tests.

Statistical considerations: The sample size estimate for this trial is determined for the primary hypothesis that the projected rate of decay of creatinine clearance (1 mL/min) in Type II diabetes mellitus patients with diabetic nephropathy (creatinine clearance <90 mL/min) is reduced by treating with triene. The study is powered to detect (80%) a 6 mL/min change in creatinine clearance over 6 months with four 2-monthly readings (i.e., 0, 2, 4, and 6 months) assuming a 10% rate of loss to follow-up at the 5% significance level.

Conclusions:

The efficacy of triene as a treatment of microvascular complications in patients with Type II diabetes mellitus is confirmed.

The safety of long-term administration of triene in patients with poor blood glucose control and diabetic nephropathy due to Type II diabetes mellitus is confirmed.

It also provides a means to determine the clinical usefulness of alternative fructosamine oxidase inhibitors such as the copper chelating compounds D-penicillamine, sar, and diamsar (i.e., triene could be used in place of placebo in ensuing clinical trials).

What is claimed is:

1. A method for treating a human for diabetes mellitus comprising administering to said human a pharmaceutically acceptable amount of a copper binding triene compound.

2. The method of claim 1 wherein said triene is administered orally.

3. The method of claim 1 wherein said triene is administered by a non-oral route.

4. The method of claim 1 wherein said administration is by injection.

5. The method of claim 1 wherein a long-acting release form of said triene is administered.

6. The method of claim 2 wherein a long-acting release form of said triene is administered.

7. The method of claim 3 wherein a long-acting release form of said triene is administered.

8. A method for treating a human for diabetes mellitus comprising orally administering to said human a triene that binds copper in an amount ranging from about 1.2 to about 2.4 grams per day.

9. The method of claim 8 wherein a long-acting release form of said triene is administered.

10. The method of claim 5 wherein about 600 milligrams to about 1200 milligrams of said triene is administered two times per day.

11. The method of claim 5 wherein about 400 milligrams to about 800 milligrams of said triene is administered three times per day.

12. The method of claim 5 wherein about 300 milligrams to about 600 milligrams of said triene is administered four times per day.

13. The method of any of claims 1–11 or 12 wherein said triene is a triene salt.

14. The method of claim 13 wherein said human has type 1 diabetes.

15. The method of claim 13 wherein said human has type 2 diabetes.

16. The method of claim 13 wherein said triene salt is a triene hydrochloride salt.

17. The method of claim 13 wherein said triene salt is a dihydrochloride salt.

18. The method of either of claims 16 or 17 wherein said human has type 1 diabetes.

19. The method of either of claims 16 or 17 wherein said human has type 2 diabetes.

20. The method of any of claims 1–11 or 12 wherein said triene is triethylenetetramine.

21. The method of claim 20 wherein said human has type 1 diabetes.

22. The method of claim 20 wherein said human has type 2 diabetes.

23. The method of claim 20 wherein said triethylenetetramine is a triethylenetetramine hydrochloride salt.

24. The method of claim 23 wherein said triethylenetetramine hydrochloride salt is triethylenetetramine dihydrochloride.

25. The method of either of claims 23 or 24 wherein said human has type 1 diabetes.

26. The method of either of claims 23 or 24 wherein said human has type 2 diabetes.

27. A method for treating a human for diabetes mellitus comprising orally administering to said human a triene that binds copper in an amount ranging from about 9 mg/kg to about 200 mg/kg per day.

28. The method of claim 27 wherein said triene is administered in a single dose or in divided doses.

29. The method of claim 28 wherein said human has type 1 diabetes.

30. The method of claim 28 wherein said human has type 2 diabetes.

31. A method for treating a human for diabetes mellitus comprising orally administering to said human a triene that binds copper in an amount ranging from about 11 mg/kg to about 100 mg/kg per day.

32. The method of claim 31 wherein said triene is administered in a single dose or in divided doses.

33. The method of claim 32 wherein said human has type 1 diabetes.

34. The method of claim 32 wherein said human has type 2 diabetes.

35. A method for treating a human for diabetes mellitus comprising orally administering to said human a triene that binds copper in an amount ranging from about 13 mg/kg to about 75 mg/kg per day.

36. The method of claim 35 wherein said triene is administered in a single dose or in divided doses.

37. The method of claim 36 wherein said human has type 1 diabetes.

38. The method of claim 36 wherein said human has type 2 diabetes.

39. A method for treating a human for diabetes mellitus comprising orally administering to said human a triene that binds copper in an amount ranging from about 15 mg/kg to about 50 mg/kg per day.

40. The method of claim 39 wherein said triene is administered in a single dose or in divided doses.

41. The method of claim 40 wherein said human has type 2 diabetes.

42. The method of claim 40 wherein said human has type 2 diabetes.

43. A method for treating a human for diabetes mellitus comprising orally administering to said human a triene that binds copper in an amount ranging from about 17 mg/kg to about 35 mg/kg per day.

44. The method of claim 43 wherein said triene is administered in a single dose or in divided doses.

45. The method of claim 44 wherein said human has type 1 diabetes.

46. The method of claim 44 wherein said human has type 2 diabetes.

47. The method of any of claims 27–45 or 46 wherein a long-acting release form of said triene is administered.

48. The method of any of claims 27–45 or 46 wherein said triene is a triene salt.

49. The method of claim 48 wherein a long-acting release form of said triene salt is administered.

50. The method of claim 48 wherein said triene salt is a triene hydrochloride salt.

51. The method of claim 48 wherein a long-acting release form of said triene hydrochloride salt is administered.

52. The method of claim 50 wherein said triene hydrochloride salt is a dihydrochloride salt.

53. The method of claim 52 wherein a long-acting release form of said triene dihydrochloride salt is administered.

54. The method of any of claims 27–45 or 46 wherein said triene is triethylenetetramine.

55. The method of claim 54 wherein a long-acting release form of said triethylenetetramine is administered.

56. The method of claim 54 wherein said triethylenetetramine is a triethylenetetramine hydrochloride salt.

57. The method of claim 56 wherein a long-acting release form of said triethylenetetramine hydrochloride salt is administered.

58. The method of claim 56 wherein said triethylenetetramine dihydrochloride salt is triethylenetetramine dihydrochloride.

59. The method of claim 58 wherein a long-acting release form of said triethylenetetramine dihydrochloride is administered.

60. A method for treating a human for diabetes mellitus comprising administering to said human a triene that binds copper in an amount ranging from about 120 milligrams to about 240 milligrams per day by a non-oral route of administration.

61. The method of claim 60 wherein said triene is administered in a single dose or in divided doses.

62. The method of claim 60 wherein said triene is administered by infusion.

63. The method of claim 60 wherein said triene is administered by injection.

64. The method of claim 60 wherein said human has type 1 diabetes.

65. The method of claim 60 wherein said human has type 2 diabetes.

66. A method for treating a human for diabetes mellitus comprising administering to said human a triene that binds copper in an amount ranging from about 0.9 mg/kg to about 20 mg/kg per day by a non-oral route of administration.

67. The method of claim 66 wherein said triene is administered in a single dose or in divided doses.

68. The method of claim 66 wherein said triene is administered by infusion.

69. The method of claim 66 wherein said triene is administered by injection.

70. The method of claim 66 wherein said human has type 1 diabetes.

71. The method of claim 66 wherein said human has type 2 diabetes.

72. A method for treating a human for diabetes mellitus comprising administering to said human a triene that binds copper in an amount ranging from about 1.1 mg/kg to about 10 mg/kg per day by a non-oral route of administration.

73. The method of claim 72 wherein said triene is administered in a single dose or in divided doses.

74. The method of claim 72 wherein said triene is administered by infusion.

75. The method of claim 72 wherein said triene is administered by injection.

76. The method of claim 72 wherein said human has type 1 diabetes.

77. The method of claim 72 wherein said human has type 2 diabetes.

78. A method for treating a human for diabetes mellitus comprising administering to said human a triene that binds copper in an amount ranging from about 1.3 mg/kg to about 7.5 mg/kg per day by a non-oral route of administration.

79. The method of claim 78 wherein said triene is administered in a single dose or in divided doses.

80. The method of claim 78 wherein said triene is administered by infusion.

81. The method of claim 78 wherein said triene is administered by injection.

82. The method of claim 78 wherein said human has type 1 diabetes.

83. The method of claim 78 wherein said human has type 2 diabetes.

84. A method for treating a human for diabetes mellitus comprising administering to said human a triene that binds copper in an amount ranging from about 1.5 mg/kg to about 5.0 mg/kg per day by a non-oral route of administration.

85. The method of claim 84 wherein said triene is administered in a single dose or in divided doses.

86. The method of claim 84 wherein said triene is administered by infusion.

87. The method of claim 84 wherein said triene is administered by injection.

88. The method of claim 84 wherein said human has type 1 diabetes.

89. The method of claim 84 wherein said human has type 2 diabetes.

90. A method for treating a human for diabetes mellitus comprising administering to said human a triene that binds copper in an amount ranging from about 1.7 mg/kg to about 3.5 mg/kg per day by a non-oral route of administration.

91. The method of claim 90 wherein said triene is administered in a single dose or in divided doses.

92. The method of claim 90 wherein said triene is administered by infusion.

93. The method of claim 90 wherein said triene is administered by injection.

94. The method of claim 90 wherein said human has type 1 diabetes.

95. The method of claim 90 wherein said human has type 2 diabetes.

96. The method of any of claims 60–94 or 95 wherein a long-acting release form of said triene is administered.

97. The method of any of claims 60–94 or 95 wherein said triene is a triene salt.

98. The method of claim 97 wherein a long-acting release form of said triene salt is administered.

99. The method of claim 97 wherein said triene salt is a triene hydrochloride salt.

100. The method of claim 99 wherein a long-acting release form of said triene hydrochloride salt is administered.

101. The method of claim 99 wherein said triene hydrochloride salt is a dihydrochloride salt.

102. The method of claim 101 wherein a long-acting release form of said triene dihydrochloride salt is administered.

103. The method of any of claims 60–94 or 95 wherein said triene is triethylenetetramine.

104. The method of claim 103 wherein a long-acting release form of said triethylenetetramine is administered.

105. The method of claim 103 wherein said triethylenetetramine is a triethylenetetramine hydrochloride salt.

106. The method of claim 103 wherein a long-acting release form of said triethylenetetramine hydrochloride salt is administered.

107. The method of claim 105 wherein said triethylenetetramine hydrochloride salt is triethylenetetramine dihydrochloride.

108. The method of claim 107 wherein a long-acting release form of said triethylenetetramine dihydrochloride is administered.

109. The method of claim 1 wherein said copper binding triene is a copper chelating agent effective to inhibit fructosamine oxidase activity.

* * * * *